(12) United States Patent
Pongpairochana et al.

(10) Patent No.: US 7,704,231 B2
(45) Date of Patent: Apr. 27, 2010

(54) HAND-HELD ELECTRONICALLY CONTROLLED INJECTION DEVICE FOR INJECTING LIQUID MEDICATIONS

(75) Inventors: Vincent Pongpairochana, La Conversion (CH); Timothy John MacLean, Bath and South East Somerset (GB); Robert Prasser, Althofen (AT); Gerhard Lauchard, Silberegg (AT); Werner Wurmbauer, Klagenfurt (AT); Gerhard Kogler, Althofen (AT)

(73) Assignee: Ares Trading S.A., Aubonne (CH)

( * ) Notice: Subject to any disclaimer, the term of this patent is extended or adjusted under 35 U.S.C. 154(b) by 299 days.

(21) Appl. No.: 10/589,465

(22) PCT Filed: Feb. 17, 2005

(86) PCT No.: PCT/EP2005/050711

§ 371 (c)(1),
(2), (4) Date: Oct. 16, 2006

(87) PCT Pub. No.: WO2005/077441

PCT Pub. Date: Aug. 25, 2005

(65) Prior Publication Data
US 2007/0197968 A1   Aug. 23, 2007

(30) Foreign Application Priority Data
Feb. 18, 2004 (EP) .................................. 04100647

(51) Int. Cl.
A61M 5/20 (2006.01)
A61M 37/00 (2006.01)
A61M 31/00 (2006.01)

(52) U.S. Cl. .......................... 604/134; 604/131; 604/67
(58) Field of Classification Search .................. 604/134
See application file for complete search history.

(56) References Cited

U.S. PATENT DOCUMENTS

| | | | |
|---|---|---|---|
| 4,150,672 A | 4/1979 | Whitney et al. |
| 4,273,122 A | 6/1981 | Whitney et al. |
| 4,373,527 A | 2/1983 | Fischell |
| 4,435,173 A | 3/1984 | Siposs et al. |
| 4,493,704 A | 1/1985 | Beard et al. |
| 4,529,401 A | 7/1985 | Leslie et al. |
| 4,573,994 A | 3/1986 | Fischell et al. |
| 4,627,835 A | 12/1986 | Fenton, Jr. |
| 4,950,246 A | 8/1990 | Muller |
| 4,959,056 A | 9/1990 | Dombrowski et al. |
| 4,976,696 A | 12/1990 | Sanderson et al. |
| 4,978,335 A | 12/1990 | Arthur, III |
| 5,034,004 A | 7/1991 | Crankshaw |
| 5,106,375 A | 4/1992 | Conero |

(Continued)

FOREIGN PATENT DOCUMENTS

DE 29 50 140 6/1981

(Continued)

*Primary Examiner*—Nicholas D Lucchesi
*Assistant Examiner*—Jason Flick
(74) *Attorney, Agent, or Firm*—Nixon Peabody LLP

(57) ABSTRACT

A hand-held, electronically controlled injection device (1) for injecting preset doses of liquid medications, having a housing (2) for receiving a cartridge (4) containing the liquid medication and having a contact surface (16) for contacting a patient's skin; and actuator elements (41) for moving the cartridge (4) within the housing (2) to and from the contact surface (16).

31 Claims, 21 Drawing Sheets

U.S. PATENT DOCUMENTS

| | | | |
|---|---|---|---|
| 5,131,816 A | 7/1992 | Brown et al. | |
| 5,139,484 A | 8/1992 | Hazon et al. | |
| 5,232,449 A | 8/1993 | Stern et al. | |
| 5,254,096 A | 10/1993 | Rondelet et al. | |
| 5,269,762 A | 12/1993 | Armbruster et al. | |
| 5,330,431 A | 7/1994 | Herskowitz | |
| 5,354,287 A | 10/1994 | Wacks et al. | |
| 5,360,410 A | 11/1994 | Wacks et al. | |
| 5,545,140 A | 8/1996 | Conero et al. | |
| 5,573,515 A | 11/1996 | Wilson et al. | |
| 5,584,815 A | 12/1996 | Pawelka et al. | |
| 5,628,309 A | 5/1997 | Brown | |
| 5,651,775 A | 7/1997 | Walker et al. | |
| 5,658,133 A | 8/1997 | Anderson et al. | |
| 5,662,612 A | 9/1997 | Niehoff | |
| 5,681,285 A | 10/1997 | Ford et al. | |
| 5,693,027 A | 12/1997 | Hansen et al. | |
| 5,697,916 A | 12/1997 | Schraga | |
| 5,704,922 A | 1/1998 | Brown | |
| 5,720,733 A | 2/1998 | Brown | |
| 5,728,074 A | 3/1998 | Castellano et al. | |
| 5,782,814 A | 7/1998 | Brown et al. | |
| 5,792,117 A | 8/1998 | Brown | |
| 5,882,343 A | 3/1999 | Wilson et al. | |
| 5,928,197 A | 7/1999 | Niehoff | |
| 5,928,201 A | 7/1999 | Poulsen et al. | |
| 5,947,934 A | 9/1999 | Hansen et al. | |
| 5,954,700 A | 9/1999 | Kovelman | |
| 5,997,513 A * | 12/1999 | Smith et al. | 604/198 |
| 6,019,745 A | 2/2000 | Gray | |
| 6,045,537 A | 4/2000 | Klitmose | |
| 6,110,152 A | 8/2000 | Kovelman | |
| 6,159,161 A | 12/2000 | Hodosh | |
| 6,171,276 B1 * | 1/2001 | Lippe et al. | 604/67 |
| 6,203,530 B1 | 3/2001 | Stewart, Sr. | |
| 6,248,090 B1 | 6/2001 | Jensen et al. | |
| 6,269,340 B1 | 7/2001 | Ford et al. | |
| 6,277,098 B1 | 8/2001 | Klitmose et al. | |
| 6,340,357 B1 | 1/2002 | Poulsen et al. | |
| 6,406,460 B1 | 6/2002 | Hogan | |
| 6,423,035 B1 | 7/2002 | Das et al. | |
| 6,547,755 B1 | 4/2003 | Lippe et al. | |
| 6,585,698 B1 | 7/2003 | Packman et al. | |
| 6,599,272 B1 * | 7/2003 | Hjertman et al. | 604/209 |
| 6,641,566 B2 | 11/2003 | Douglas et al. | |
| 6,645,177 B1 | 11/2003 | Shearn | |
| 6,685,678 B2 | 2/2004 | Evans et al. | |
| 6,830,560 B1 | 12/2004 | Gross et al. | |
| 6,942,646 B2 | 9/2005 | Langley et al. | |
| 6,954,697 B1 | 10/2005 | Smith | |
| 6,972,007 B2 | 12/2005 | Geiser et al. | |
| 6,997,906 B2 | 2/2006 | Langley et al. | |
| 7,001,360 B2 | 2/2006 | Veasey et al. | |
| 7,008,405 B2 | 3/2006 | Langley et al. | |
| 7,052,484 B2 | 5/2006 | Veasey et al. | |
| 2002/0030002 A1 | 3/2002 | Verkaart et al. | |
| 2002/0032429 A1 | 3/2002 | Hjertman et al. | |
| 2002/0128606 A1 | 9/2002 | Cowan et al. | |
| 2002/0133113 A1 | 9/2002 | Madsen et al. | |
| 2003/0060768 A1 | 3/2003 | Kiyatake et al. | |
| 2003/0065287 A1 * | 4/2003 | Spohn et al. | 604/154 |
| 2003/0093036 A1 | 5/2003 | Crossman et al. | |
| 2003/0153868 A1 | 8/2003 | Azizi et al. | |
| 2003/0163090 A1 | 8/2003 | Blomquist et al. | |
| 2004/0176729 A1 | 9/2004 | Langley et al. | |
| 2004/0178255 A1 | 9/2004 | Eich et al. | |
| 2004/0210199 A1 | 10/2004 | Atterbury et al. | |
| 2004/0249348 A1 | 12/2004 | Wimpenny et al. | |
| 2004/0260247 A1 | 12/2004 | Veasey et al. | |
| 2005/0004529 A1 | 1/2005 | Veasey et al. | |
| 2005/0090781 A1 * | 4/2005 | Baba et al. | 604/209 |
| 2005/0107899 A1 | 5/2005 | Steffen | |
| 2005/0107923 A1 * | 5/2005 | Vanderveen | 700/282 |
| 2005/0113765 A1 | 5/2005 | Veasey et al. | |
| 2005/0148938 A1 | 7/2005 | Blomquist | |
| 2005/0151652 A1 | 7/2005 | Frasch | |
| 2005/0182360 A1 | 8/2005 | Yeandel et al. | |
| 2005/0251103 A1 | 11/2005 | Steffen et al. | |
| 2007/0142776 A9 * | 6/2007 | Kovelman et al. | 604/136 |

FOREIGN PATENT DOCUMENTS

| | | |
|---|---|---|
| DE | 38 24 217 | 1/1990 |
| DE | 44 20 232 | 12/1995 |
| DE | 196 43 913 | 4/1998 |
| DE | 19643813 | 4/1998 |
| DE | 102 36 669 | 2/2004 |
| EP | 0 362 484 | 4/1990 |
| EP | 0 319 279 | 3/1992 |
| EP | 1 219 312 | 7/2002 |
| EP | 1 462 134 | 9/2004 |
| EP | 1 593 403 | 11/2005 |
| EP | 1 666 080 | 6/2006 |
| GB | 809 773 | 3/1959 |
| GB | 2262452 | 6/1993 |
| JP | 2004-100838 | 4/2004 |
| WO | WO 93/012726 | 7/1993 |
| WO | WO 95/009021 | 4/1995 |
| WO | WO 96/038190 | 12/1996 |
| WO | WO 97/014459 | 4/1997 |
| WO | WO 99/065548 | 12/1999 |
| WO | WO 02/11792 | 2/2002 |
| WO | WO 02/081011 | 10/2002 |
| WO | WO 03/047663 | 6/2003 |
| WO | WO 03/057286 | 7/2003 |
| WO | WO 03/077968 | 9/2003 |
| WO | WO 2004/006995 | 1/2004 |
| WO | WO 2004/047891 | 6/2004 |
| WO | WO 2004/084795 | 10/2004 |
| WO | WO 2005/000384 | 1/2005 |
| WO | WO 2005/004954 | 1/2005 |
| WO | WO 2005/032449 | 4/2005 |
| WO | WO 2006/015501 | 2/2006 |
| WO | WO 2006/058883 | 6/2006 |
| WO | WO 2006/069455 | 7/2006 |

* cited by examiner

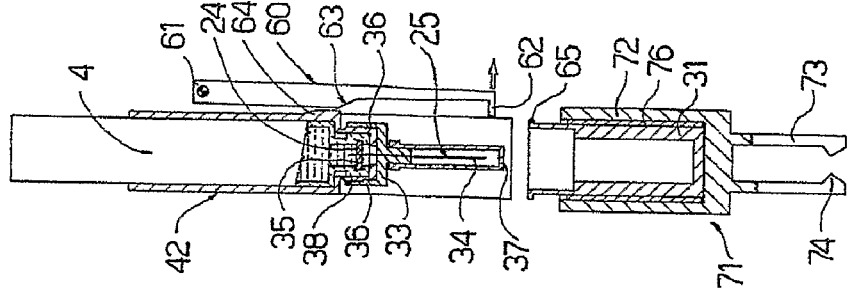
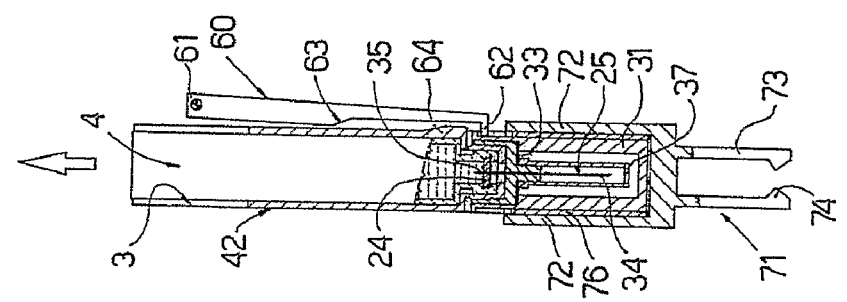
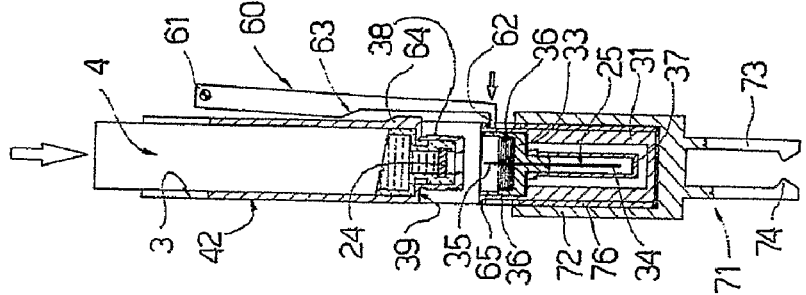
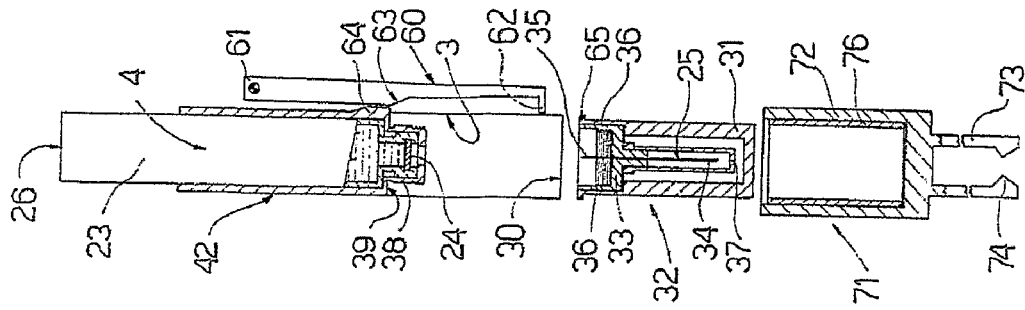

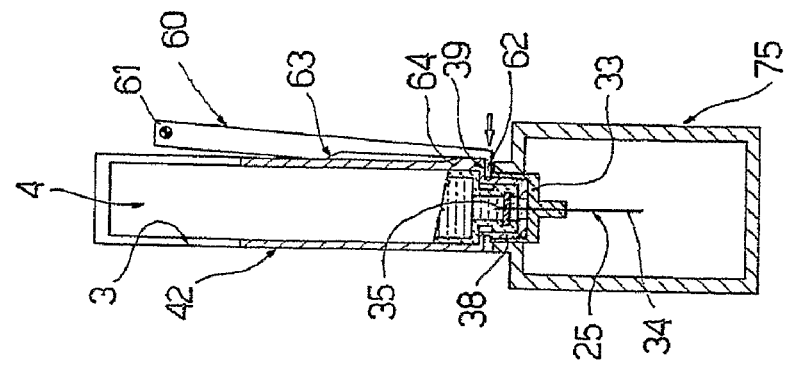
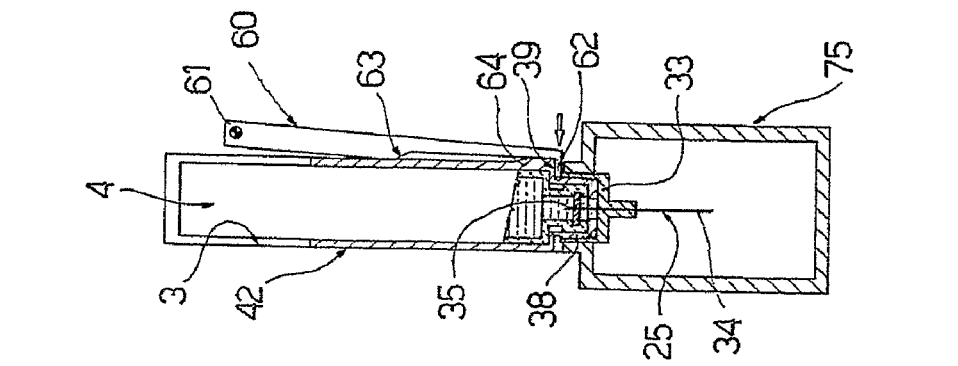
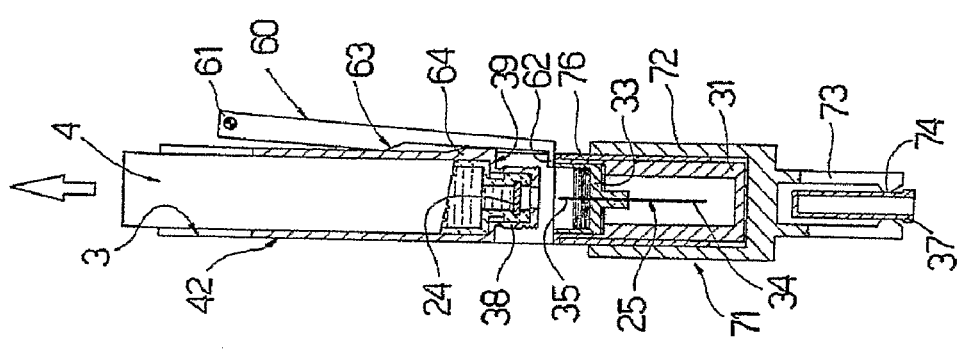
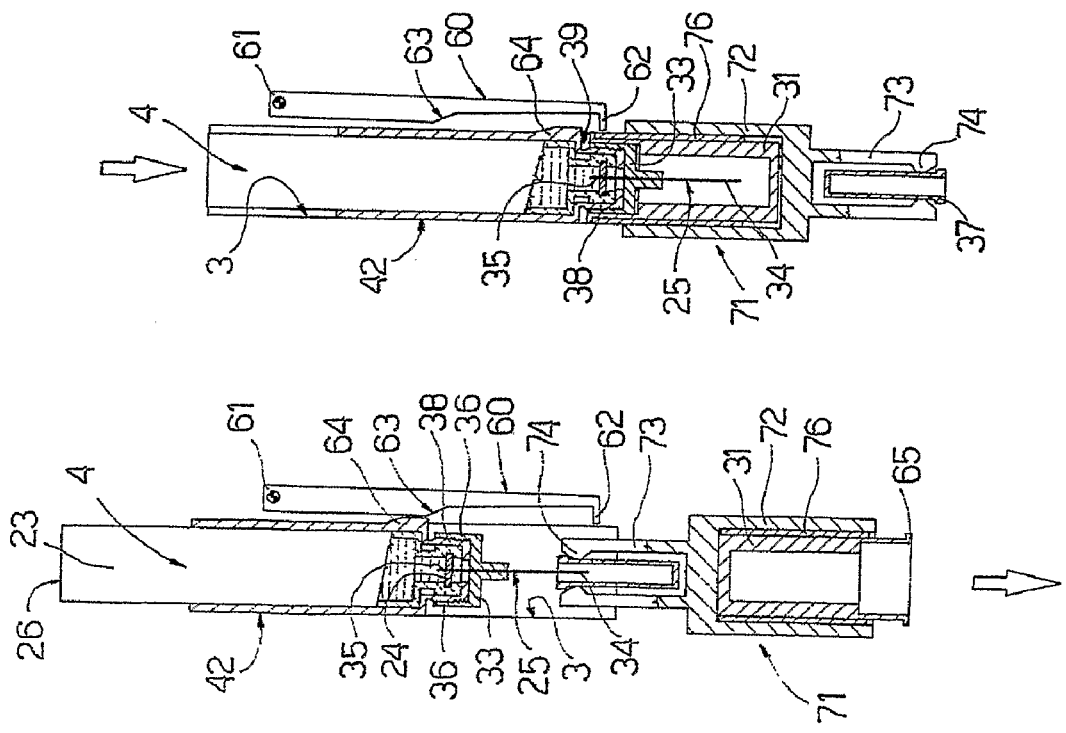

Fig.21
Fig.22
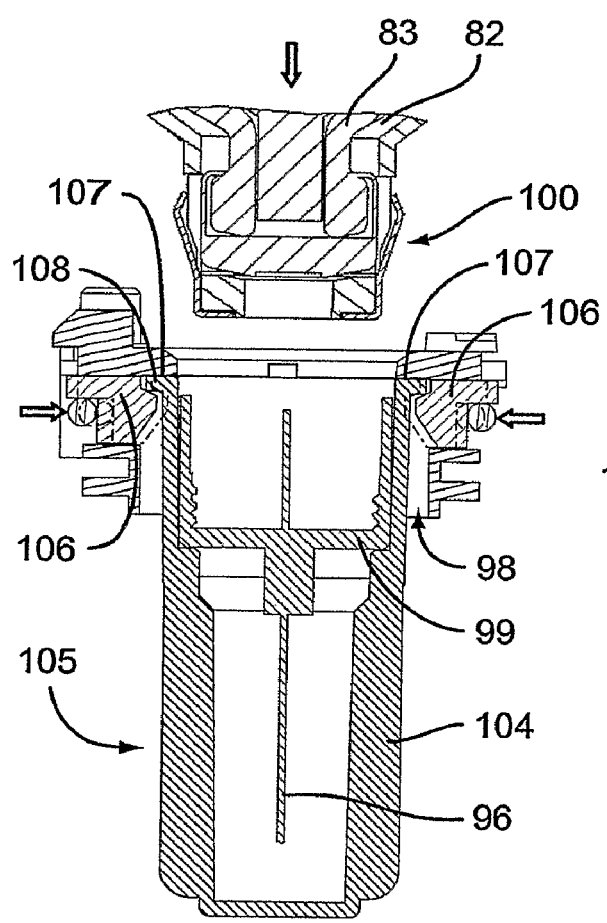
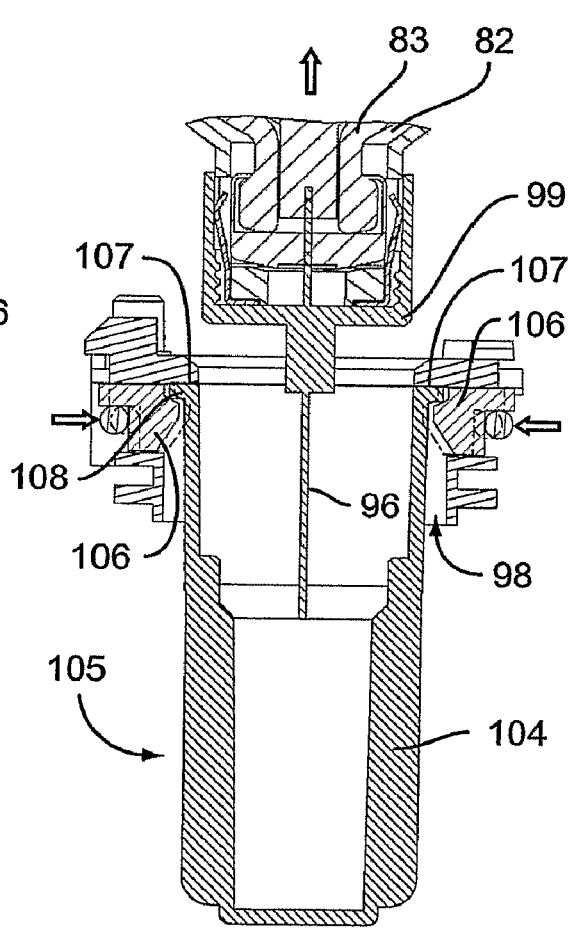

Fig.24
Fig.25
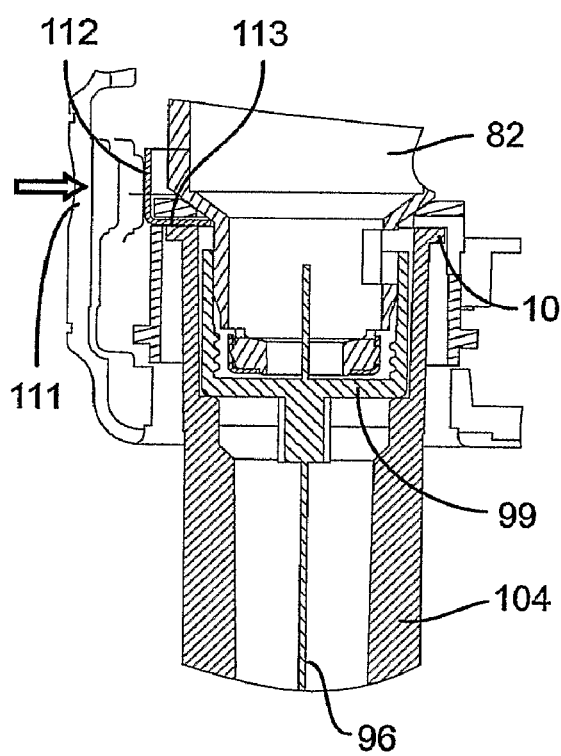
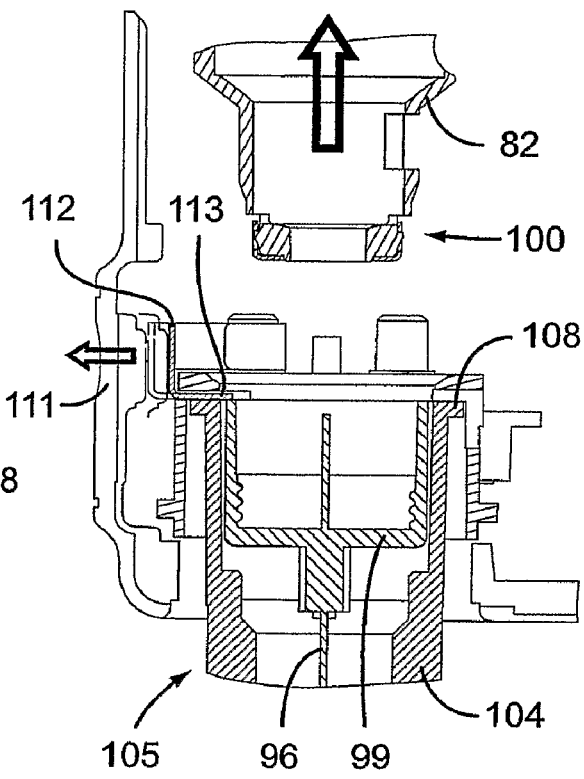

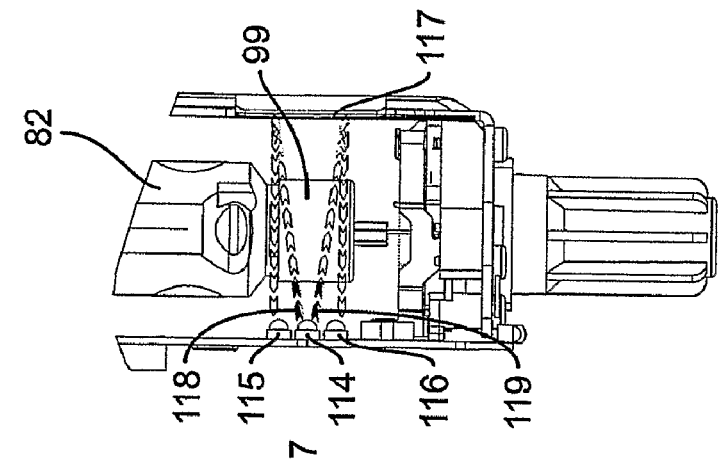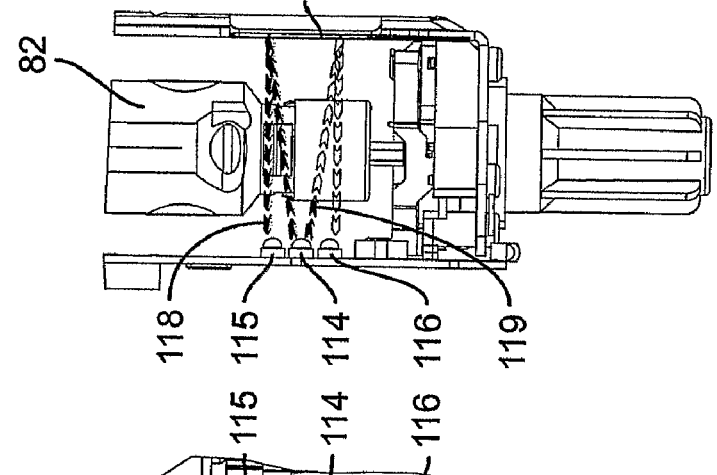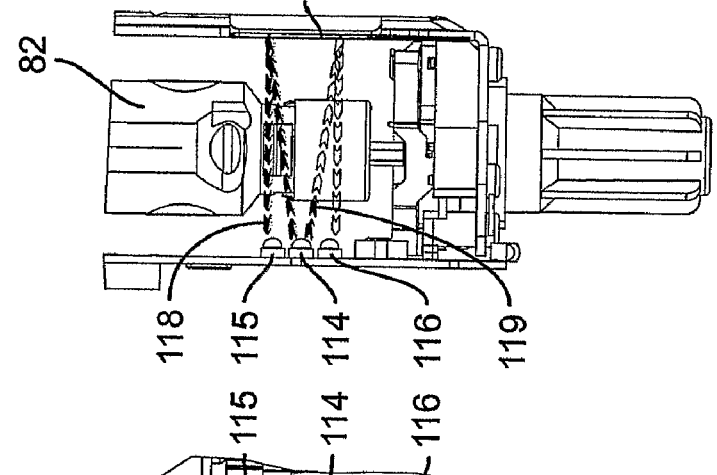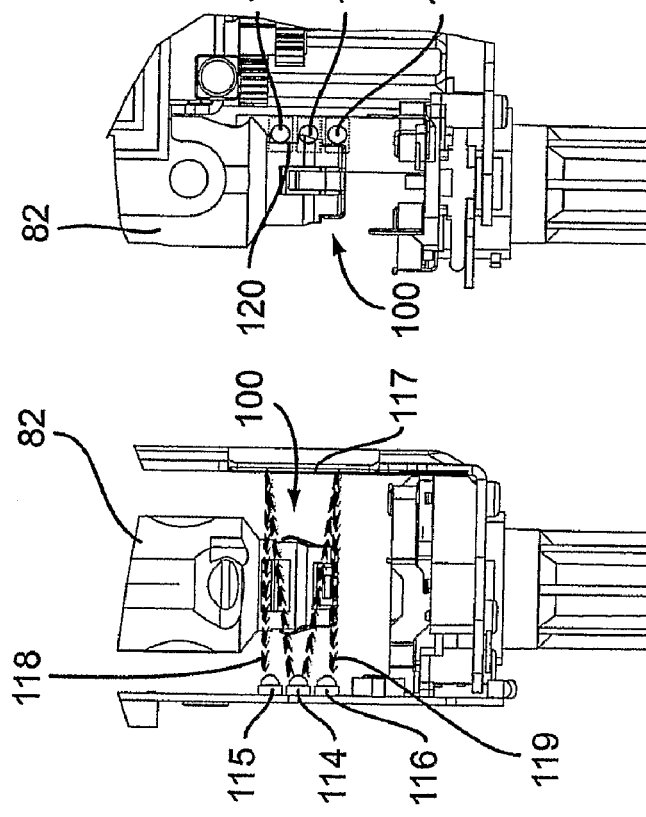

HAND-HELD ELECTRONICALLY CONTROLLED INJECTION DEVICE FOR INJECTING LIQUID MEDICATIONS

TECHNICAL FIELD

The present invention relates to a hand-held, electronically controlled injection device for injecting liquid medications, and in particular of the type for performing subcutaneous injections fully automatically.

BACKGROUND ART

As is known, certain types of diseases, such as diabetes, call for injecting medications, such as insulin, several times a day, and the medication dosage to be injected may vary from one patient to another, and, for the same patient, during the day and from one day to another.

Over the past few years, therefore, electronically controlled injection devices have been devised and widely used to permit self-injection of medications in the required doses.

Patent Application US-A-2002/0133113 describes one such injection device substantially comprising a hand-held housing, which houses a cartridge containing the liquid medication for injection, and defines, on a contact surface for contacting the patient's skin, a through opening by which to fit a disposable needle to one end of the cartridge. The injection device also comprises an electromechanical actuator assembly, which is activated selectively to slide a plunger hermetically inside the cartridge body and deliver the liquid medication through the needle into the patient's skin.

Operation of the injection device is controlled by a programmable microprocessor, which receives signals from various switches and buttons—e.g. one or more medication dose selection buttons and an injection start button—and generates signals by which to control the actuator assembly according to a program stored in the microprocessor.

The injection device described therefore provides for selecting each medication dose for injection, and delivering the dose automatically.

Though functionally valid, the above type of injection device still leaves room for further improvement. More specifically, a need is felt for solutions designed to further reduce the amount of human intervention required, and to further safeguard users, with no medical experience, in preparing and self-injecting medications.

DISCLOSURE OF INVENTION

It is an object of the present invention to provide an electronically controlled injection device for injecting liquid medications, designed to meet the above requirement, and which in particular provides for preparing and performing subcutaneous injections fully automatically.

According to the present invention, there is provided a hand-held, electronically controlled injection device for injecting preset doses of liquid medications, comprising a housing which is adapted for receiving a medication container containing the liquid medication, and has a contact surface for contacting a patient's skin, characterized by comprising first actuator means for moving said medication container within said housing to and from said contact surface.

BRIEF DESCRIPTION OF THE DRAWINGS

A preferred, non-limiting embodiment of the present invention will be described by way of example with reference to the accompanying drawings, in which:

FIGS. 4, 5, 6, 7 and 8 show a portion of the FIG. 1 injection device illustrating assembly of a disposable needle;

FIGS. 9, 10 and 11 are similar to FIGS. 4-8, and illustrate removal of the needle from the injection device according to the first embodiment of the invention;

FIGS. 19 to 22 are section views showing a process of connecting the needle to the cartridge;

FIGS. 23 to 25 are section views showing a process of disconnecting the needle from the cartridge;

FIGS. 26 to 29 show an interior portion of the injection device according to the second embodiment, including sensor means for sensing connection of a needle to a cartridge;

BEST MODE FOR CARRYING OUT THE INVENTION

Figure 1:
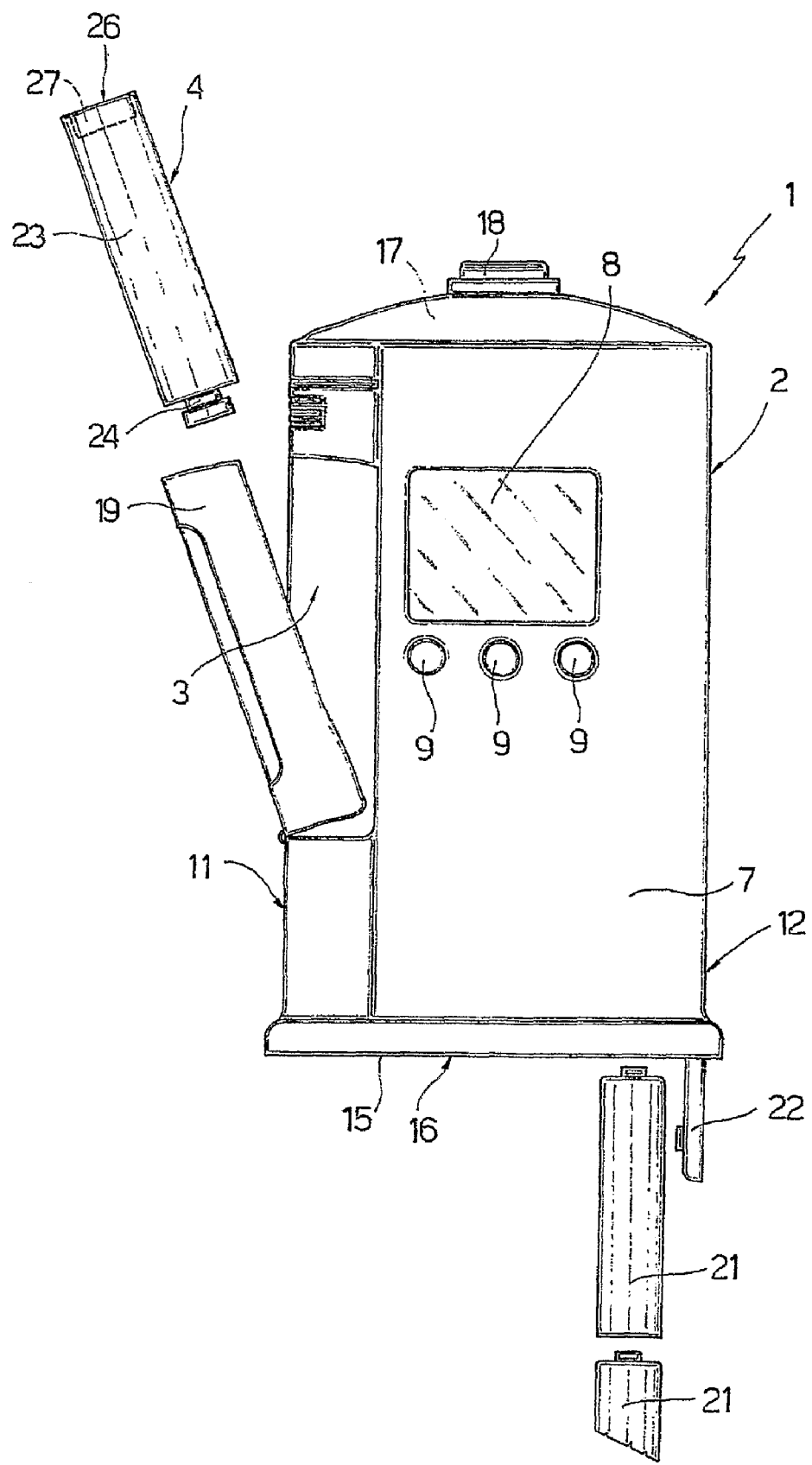
FIG. 1 shows a front view of an injection device in accordance with a first embodiment of the present invention.

Number 1 in FIG. 1 indicates as a whole a hand-held, electronically controlled injection device for injecting liquid medications, and in particular for performing subcutaneous injections fully automatically.

Injection device 1 substantially comprises a hand-held housing 2 defining a seat 3 for receiving a cartridge 4 containing the liquid medication; an injection driving unit 5 (FIGS. 2 and 3) housed inside housing 2 and selectively activated to cooperate with cartridge 4 and inject the patient with a preset dose of medication; and an electronic control unit 6 (FIG. 12)—in the example shown, a microprocessor—also housable inside housing 2 to control operation of injection driving unit 5.

More specifically, housing 2, in the example shown, is of thin prismatic shape, and comprises a front wall 7 fitted with an LCD display 8 and set-up buttons 9 (operation of which is described in detail later on); a rear wall 10; two sides 11, 12; a bottom wall 15 defining a contact surface 16 for contacting the patient's skin; and a top wall 17 fitted with an injection start button 18, as explained in detail later on.

As shown in FIG. 1, one of the sides (11) of housing 2 has a door 19 hinged at the bottom about an axis perpendicular to front wall 7 and rear wall 10, and which opens outwards to permit insertion of cartridge 4 inside seat 3.

In the example shown, seat 3 for receiving cartridge 4 has an axis A perpendicular to bottom wall 15 and top wall 17, and is formed close to side 11.

Close to the opposite side 12, housing 2 also defines a seat 20 (FIGS. 1 to 3) having an axis parallel to axis A, and for receiving one or more batteries 21 for electrically powering injection device 1, and which are inserted through a further door 22 formed in bottom wall 15.

As shown in FIGS. 1 to 11, cartridge 4 is defined by a hollow cylindrical body 23 containing a predetermined quantity of liquid medication, and having a closed, small-section end 24, through which a commonly marketed disposable needle 25 is insertable in known manner, and an open opposite end 26 engaged in fluidtight manner by a disk-shaped member or plunger 27, which is activated by injection driving unit 5 to slide inside body 23 and deliver the medication through needle 25.

Cartridge 4 is inserted inside housing 2 with end 24 for needle 25 facing bottom wall 15 and, therefore, contact surface 16 for contacting the patient's skin; and bottom wall 15 has a through opening 30, of axis A, by which to fit and remove needle 25 to/from cartridge 4, and through which needle 25 is ejected to inject the skin.

Cartridge 4 has known external markings (not shown), e.g. bar codes, notches, conducting or reflecting material in a predetermined pattern, etc., by which to determine the presence of cartridge 4 inside housing 2, and to obtain information relating to the medication, such as composition, concentration, expiry date, etc. Another possibility for identifying cartridge 4 is to use a radio frequency identification system.

As shown clearly in FIGS. 4 to 6, needle 25 is supplied in a protective needle housing 31 to prevent injury to the user, and defines, with needle housing 31, a needle assembly 32.

More specifically, needle 25 is fixed to and projects from a plastic needle support 33 which fits onto end 24 of body 23 of cartridge 4.

As is known, needle 25 comprises a front portion 34 (at the bottom in FIGS. 2 to 11) for piercing the patient's skin and which projects from needle support 33; and a rear end 35 (at the top in FIGS. 4 to 11) enclosed in needle support 33 and which fits through end 24 of body 23 of cartridge 4. More specifically, needle support 33 comprises a number of elastic flanges surrounding rear end 35 of needle 25, and which engage end 24 of body of cartridge 4 as described in detail later on.

As an alternative not shown, the reverse arrangement of the engagement between the needle support and the cartridge end is also possible; in this latter case, the cartridge end may be provided with elastic flanges engaging the needle support. This further embodiment has the advantage that the needle support need not be specially designed with elastic flanges, but rather a standard commercially available needle assembly may be used (even one with screw threads, which is a common commercially available version).

Needle housing 31 is defined by a cylindrical, cup-shaped body housing front portion 34 of needle 25, and the open end of which is fitted to needle support 33. In the example shown, needle assembly 32 also comprises an inner needle housing 37 covering front portion 34 of needle 25.

Figure 2:
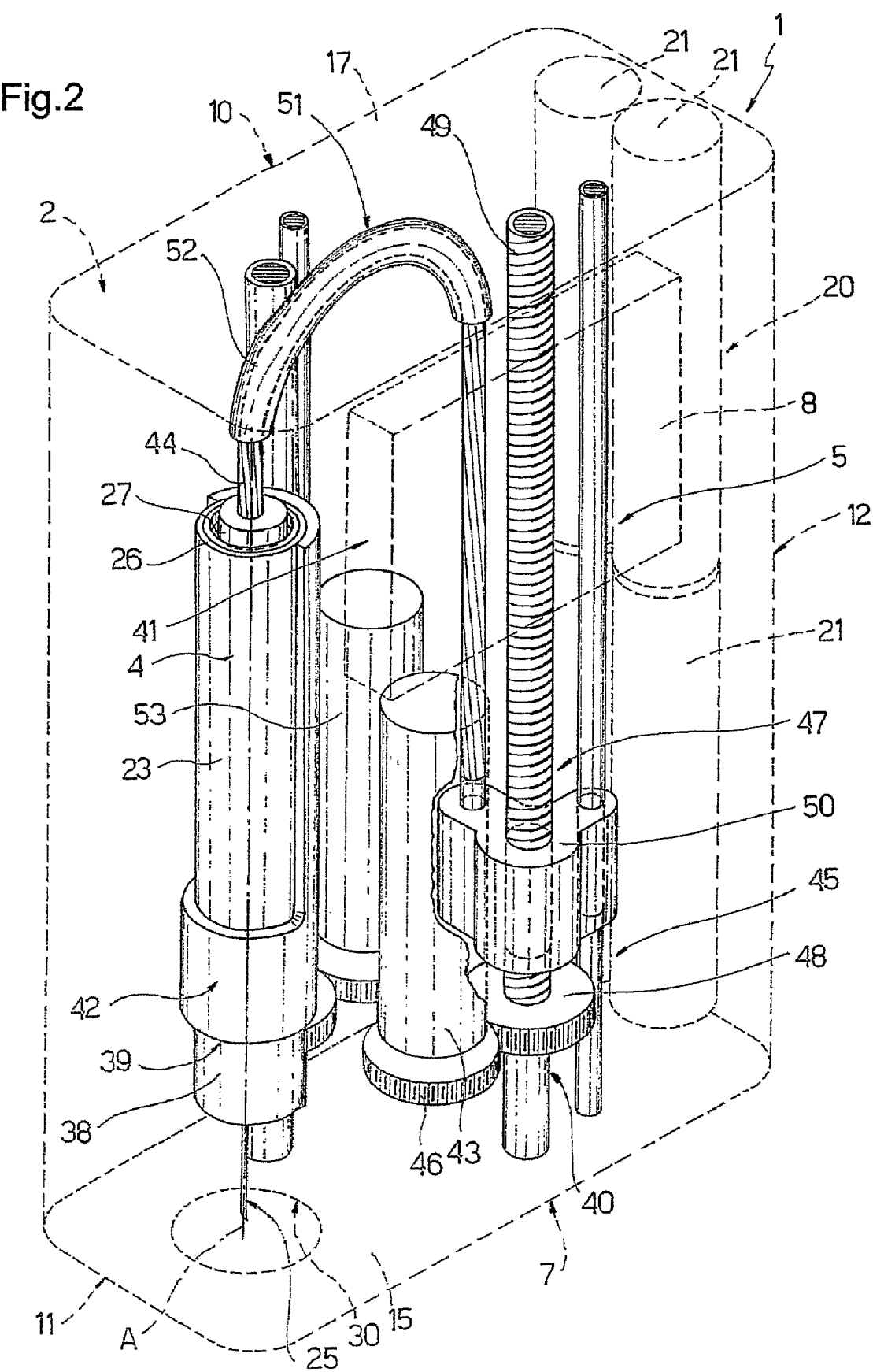
FIGS. 2 and 3 show, with parts removed for clarity, larger-scale views in perspective, from opposite sides, of the internal components of the FIG. 1 injection device.
Figure 3:
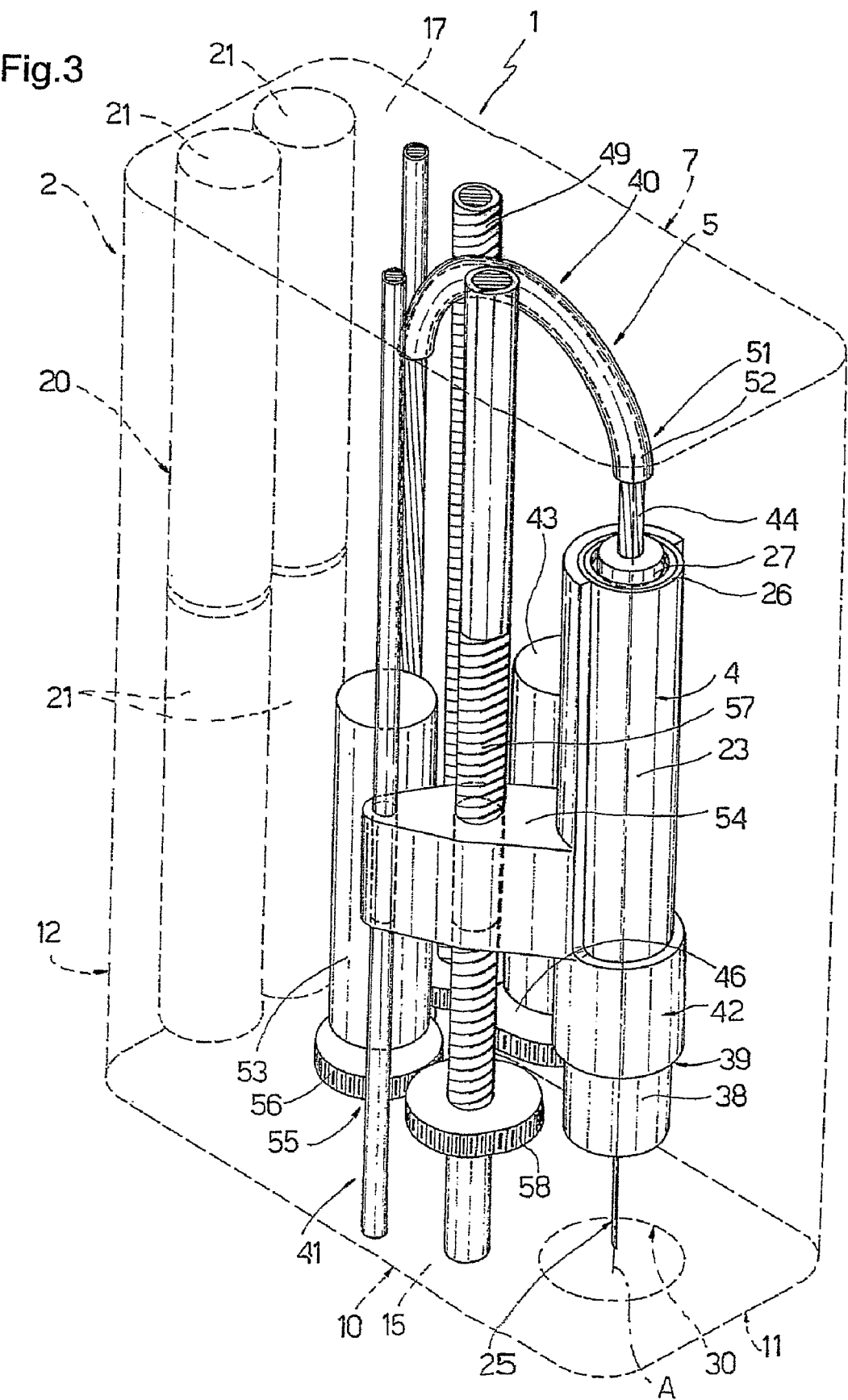

With reference to FIGS. 2 and 3, injection driving unit 5 comprises an electromechanical actuator assembly 40, which is selectively activated to act on plunger 27 of cartridge 4 and move it, inside body 23 of cartridge 4, towards end 24 to deliver the liquid medication through needle 25.

According to an important aspect of the present invention, injection driving unit 5 comprises a further electromechanical actuator assembly 41 for moving cartridge 4, inside housing 2 and along axis A, to and from contact surface 16 to automatically fit and remove needle 25 to/from cartridge 4, and to insert needle 25 inside the patient's skin at a predetermined speed.

More specifically, cartridge 4 is fitted to a supporting sleeve 42 which slides axially inside seat 3 of housing 2.

As shown in FIGS. 2 and 3, supporting sleeve 42 is open, not only at opposite axial ends, but also on the side facing door 19 to permit insertion of cartridge 4.

More specifically, supporting sleeve 42 comprises a small-section bottom end portion 38 for receiving end 24 of cartridge 4, and which, when fitting needle 25 to cartridge 4, is engaged by elastic flanges 36 of needle support 33. End portion 38 also defines an annular shoulder 39 with the rest of supporting sleeve 42.

Actuator assembly 40 comprises an electric gear motor 43; a push member 44 which acts on plunger 27 of cartridge 4 to move it, inside body 23 of cartridge 4, towards end 24; and a transmission 45 for converting the rotation generated by gear motor 43 into translation of push member 44.

More specifically (FIG. 2), transmission 45 substantially comprises a pinion 46 fitted to the output member of gear motor 43; a screw assembly 47 connected to push member 44; and an intermediate gear 48 having external teeth meshing with pinion 46, and internal teeth engaging a leadscrew 49 of screw assembly 47.

More specifically, leadscrew 49 is fitted to housing 2 to rotate but not translate axially; and screw assembly 47 also comprises a nut screw 50 fitted to leadscrew 49, integral with push member 44, and fitted to housing 2 to translate along, but not rotate with respect to, leadscrew 49.

Push member 44 is advantageously defined by the core of a known Bowden-type flexible cable 51, the sheath 52 of which has a portion fixed to housing 2, e.g. to top wall 17.

Actuator assembly 41 comprises an electric gear motor 53; a slide 54 integral with supporting sleeve 42 of cartridge 4 and movable parallel to axis A; and a transmission 55 for converting the rotation generated by gear motor 53 into translation of slide 54.

More specifically (FIG. 3), slide 54 is defined by a nut screw projecting laterally from supporting sleeve 42 and fitted to housing 2 to translate along, but not rotate with respect to, an axis parallel to axis A. Transmission 55 comprises a pinion 56 fitted to the output member of gear motor 53; a leadscrew 57 connected to slide 54 and fitted to housing 2 to rotate about, but not translate along, its own axis; and an intermediate gear 58 having external teeth meshing with pinion 56, and internal teeth engaging leadscrew 57.

With reference to FIGS. 4 to 11, injection device 1 also comprises two or more retaining elements 60 extending about seat 3 to keep needle assembly 32 fitted to housing 2 in a predetermined position (FIG. 5), in which needle assembly 32 projects along axis A from bottom wall 15 of housing 2, and the portion having needle support 33 engages opening 30 in wall 15.

More specifically, retaining elements 60 are defined by levers extending parallel to axis A and having top ends 61 hinged to a structural portion of housing 2, and free bottom ends having locking flanges 62. More specifically, locking flanges 62 are located at opening 30, and extend perpendicular to axis A and inwards of opening 30.

Retaining elements 60 are loaded elastically inwards of seat 3 to assume a lock configuration (FIGS. 5, 6, 10 and 11), and are parted into a release configuration (FIGS. 4, 7, 8 and 9) by respective cam profiles 63 interacting with a contoured annular projection 64 on supporting sleeve 42, as supporting sleeve 42 moves along axis A.

More specifically, supporting sleeve 42 and, with it, cartridge 4 are movable jointly by actuator assembly 41 in opposite directions along axis A to assume three distinct positions, namely:

a top limit position (FIGS. 4 and 7) in which cartridge 4 is loaded and any automatic operation of injection device 1 (in this case, assembling and removing needle 25, and injecting the patient with medication) starts and ends;

a bottom limit position (FIGS. 10 and 11) in which needle 25 is removed from cartridge 4; and an operating position (FIG. 6), close to the bottom limit position, in which the liquid medication is delivered through the patient's skin, and needle 25 is connected to cartridge 4.

As shown in FIGS. 4 to 11, the cam profile 63 of each retaining element 60 and the projection 64 on sleeve support 42 are in the form of complementary ramps and designed to cooperate mutually to part retaining elements 60 in and close to the top limit position of supporting sleeve 42, and to detach from each other, leaving retaining elements 60 subjected solely to the elastic return force towards axis A, in the other positions assumed by supporting sleeve 42 during its movement.

As shown in FIGS. 5 and 6, in the lock configuration, locking flanges 62 of retaining elements 60 cooperate with an outer rib 65, formed at the open end of needle housing 31, to retain needle assembly 32 inside opening 30 in bottom wall 15 as supporting sleeve 42 moves into the operating position, so that end portion 38 of supporting sleeve 42 fits inside the elastic flanges of needle support 33, and the rear end 35 of needle 25 is inserted inside end 24 of cartridge 4.

As supporting sleeve 42 moves subsequently from the operating position to the top limit position, locking flanges 62 of retaining elements 60, still in the lock configuration, press on needle housing 31 to prevent it following needle 25, needle support 33 and inner needle housing 37 moving together with supporting sleeve 42, so that needle 25 and needle support 33 can be connected to cartridge 4 and withdrawn from needle housing 31 automatically.

One will note that retaining elements 60, as they press on needle housing 31, lock needle housing 31 with respect to the user too. Thus, untimely removal of needle housing 31 by the user, e.g. as needle 25 is being connected to cartridge 4, is prevented.

In the bottom limit position of supporting sleeve 42 (FIGS. 10 and 11), locking flanges 62 of retaining elements 60 engage the gap between shoulder 39 of supporting sleeve 42 and the rear end of needle support 33 to arrest needle support 33 as supporting sleeve 42 subsequently moves into the top limit position, so that needle 25 and needle support 33 are withdrawn automatically from cartridge 4 after use.

Figure 12:
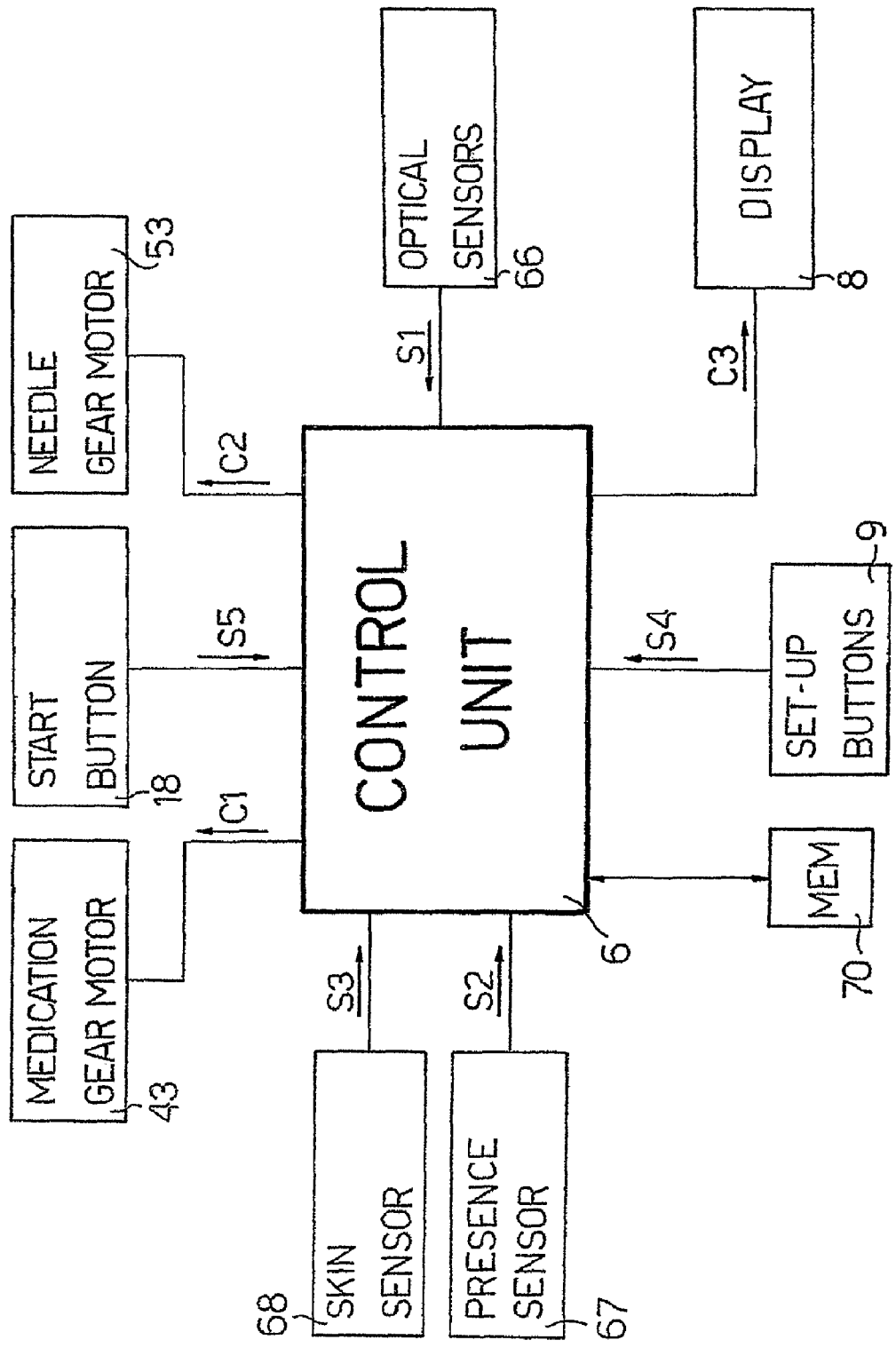
FIG. 12 shows a block diagram illustrating operation of a control unit for controlling the FIG. 1 injection device.
Figure 13:
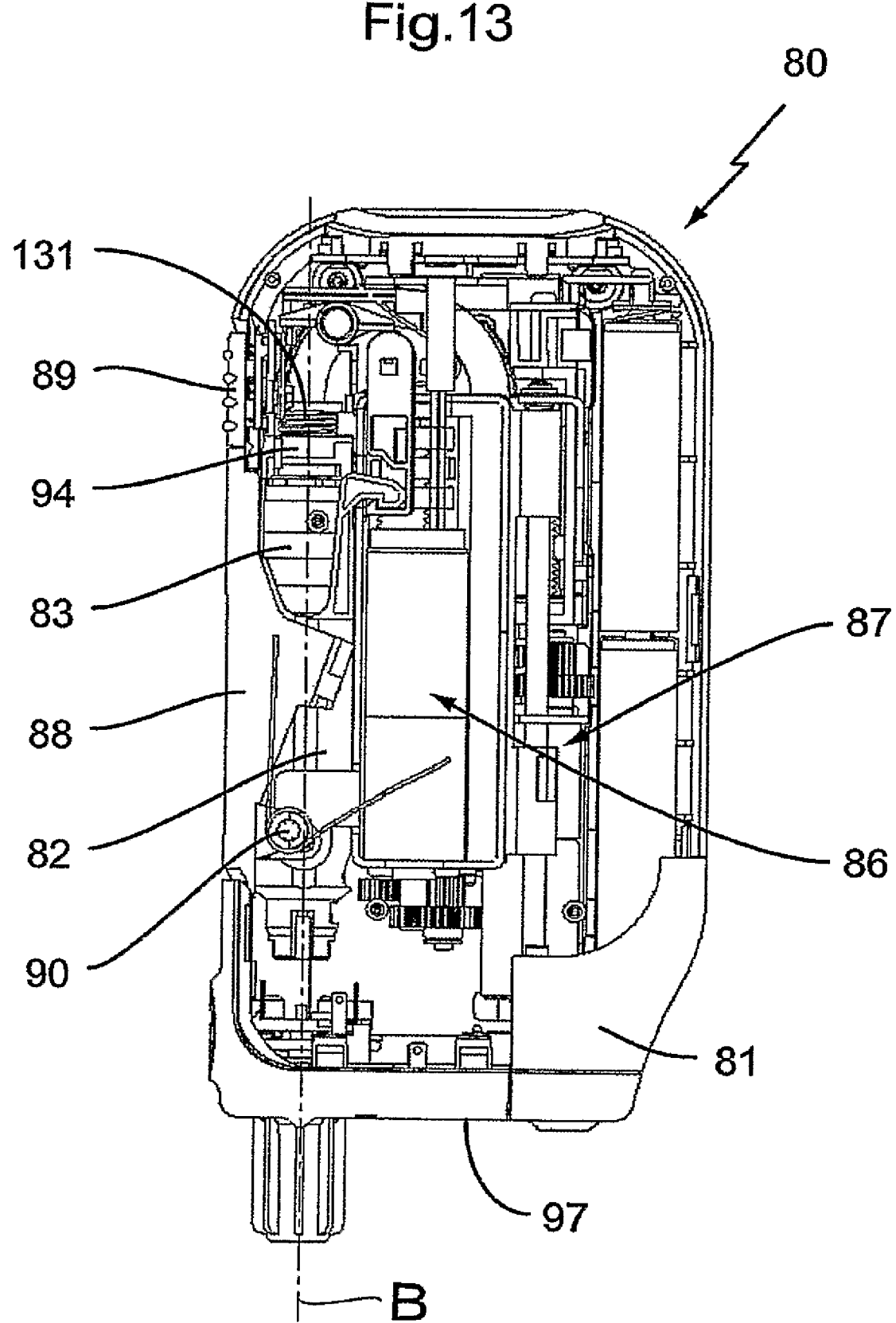
FIGS. 13 and 14 are front views of an injection device according to a second embodiment of the invention, with a front wall removed to show the interior of the device.
Figure 14:
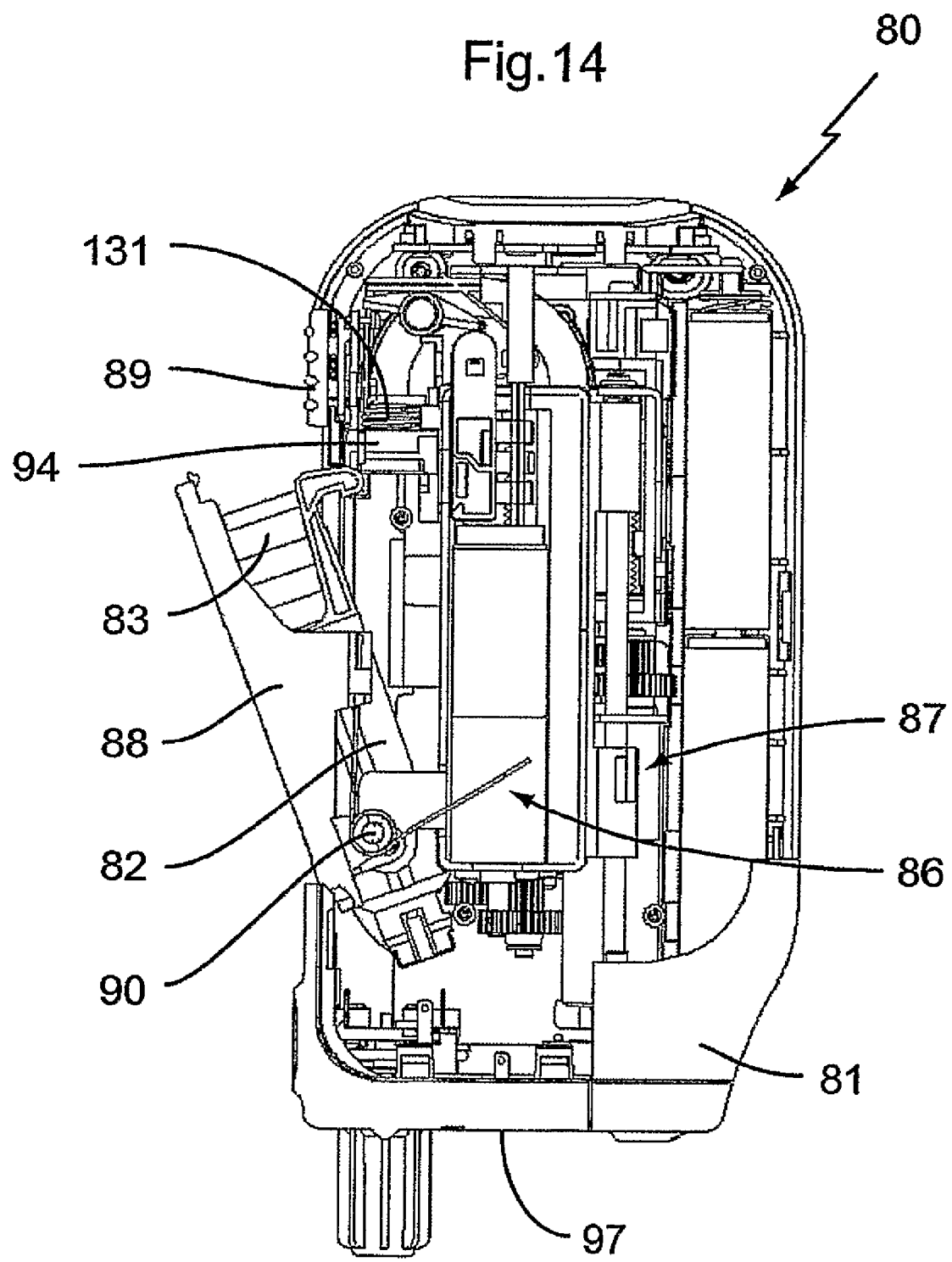

With reference to FIG. 12, control unit 6 receives a number of signals from various detecting elements and buttons on injection device 1, and supplies control signals for gear motors 43, 53 and display 8, according to a program stored in control unit 6 itself.

More specifically, control unit 6 receives the following signals:

signals S1 from sensors 66 (e.g. optical, electrical, radio-frequency, infra-red, etc.) facing seat 3 and for detecting the markings on cartridge 4;

a signal S2 from a presence sensor 67, e.g. a contact switch, located at opening 30 in bottom wall 15 and for determining engagement of the opening by an outer body of predetermined diameter, e.g. needle housing 31;

a signal S3 from a skin sensor 68, e.g. a mechanical or capacitive sensor, located on bottom wall 15 of housing 2 and for determining contact with the patient's skin;

signals S4 from set-up buttons 9, by which to select, for example, the dose for injection, the speed at which needle 25 penetrates the patient's skin, medication delivery speed, etc; and a signal S5 from injection start button 18.

On the basis of the incoming signals, control unit 6 supplies signals C1 and C2 for controlling respective gear motors 43, 53 in both rotation directions, and a signal C3 for controlling display 8.

Control unit 6 has its own internal memory 70 (shown externally for the sake of simplicity) which stores the action program of control unit 6 and the doses and timing of the injections performed, so as to inform the patient and/or doctor of these and the number of doses left in cartridge 4. The doctor can therefore check patient compliance.

Injection device 1 is also provided with an interface (known per se and not shown), e.g. a USB port, a Bluetooth communication, a infra-red port, etc., that allows information exchange with a computer for data analysis.

Programming of injection device 1 may also be possible (for example by uploading from a computer), which may be useful for clinic trials (for example, permitting injection only of certain amounts and at certain times/intervals).

Operation of injection device 1 will be described as of the FIG. 4 configuration, in which supporting sleeve 42 has no needle 25 and is set to the top limit position, and cartridge 4 has been inserted through door 19 into seat 3 of housing 2 and connected to supporting sleeve 42.

Assembly of needle 25 to cartridge 4 is controlled fully automatically by control unit 6, and is activated by simply inserting needle assembly 32, by the open end of needle housing 31, inside opening 30 in bottom wall 15 of housing 2. Insertion of the needle assembly is immediately detected by presence sensor 67, so that control unit 6 activates gear motor 53 in the direction designed, via transmission 55 and slide 54, to move supporting sleeve 42 into the operating position.

As a result of the above movement of supporting sleeve 42, projection 64 is detached from cam profiles 63, so that retaining elements 60 move inwards of opening 30, and locking flanges 62 close onto needle housing 31 to lock it in position partly engaging opening 30 (FIG. 5).

Needle assembly 32 can be inserted inside opening 30 either by hand or using an adapter indicated as a whole by 71 in FIGS. 4 to 10.

More specifically, adapter 71 is double-cup-shaped, and comprises opposite portions 72, 73 of different diameters defining respective cavities open on opposite sides and for housing needle housing 31 and inner needle housing 37 respectively. The larger-section portion 72 also houses a cylindrical slip sleeve 76 defining the actual seat for needle housing 31, and the function of which is explained later on; and the smaller-section portion 73 is provided internally, close to the open end, with an inner rib 74 which presses on inner needle housing 37 to remove it from the assembly defined by needle 25 and needle support 33.

As supporting sleeve 42 reaches the operating position (FIG. 6), end portion 38 is inserted between elastic flanges 36 and connected to needle support 33, and the rear end 35 of needle 25 is inserted inside end 24 of cartridge 4.

At this point, the rotation direction of gear motor 53 is inverted, and supporting sleeve 42 moves from the operating position to the top limit position. As it does so, needle support 33, needle 25 and, with it, inner needle housing 37 are withdrawn axially from needle housing 31 locked partly engaging opening 30 by retaining elements 60.

Close to the top limit position, projection 64 on supporting sleeve 42 interacts with cam profiles 63 of retaining elements 60 to part retaining elements 60, so that locking flanges 62 move outwards of opening 30 to release needle housing 31 (FIG. 7).

Once supporting sleeve 42 reaches the top limit position, adapter 71 can be inserted through opening 30 into seat 3 by portion 73, the cavity of which is thus engaged by inner needle housing 37. Given its smaller diameter, insertion of portion 73 is not detected by presence sensor 67. When adapter 71 is extracted from opening 30, inner needle housing 37 is removed from needle 25 (FIG. 8).

Consent to start the actual injection is given by surface 16 contacting the patient's skin and so activating skin sensor 68.

When start button 18 is pressed, gear motor 53 is first activated and, via transmission 55, moves supporting sleeve 42 back into the operating position, so that needle 25 penetrates the patients skin. Gear motor 43 is then activated and, via transmission 45 and push member 44, acts on plunger 27 of cartridge 4 to slide it towards end 24 and deliver a predetermined dose of liquid medication.

Before the injection is performed, the dose to be injected, the speed at which needle 25 penetrates the patient's skin, the speed at which the liquid medication is delivered and the injection depth can be selected using set-up buttons 9 and displayed on display 8.

Once the injection is completed, supporting sleeve 42 moves back into the top limit position.

Needle 25 can be removed from cartridge 4 fully automatically using adapter 71 (FIGS. 9 and 10), or directly using a needle box 75 (FIG. 11), e.g. of the type known by the trade name "SHARPS BOX".

More specifically, when using adapter 71 used to remove needle housing 31 and inner needle housing 37 (FIGS. 9 and 10), slip sleeve 76 must first be extracted from portion 72 to rest axially on rib 65 of needle housing 31.

At this point, needle housing 31 and the extracted part of slip sleeve 76 are inserted through opening 30 in housing 2 to activate presence sensor 67, so that control unit 6 activates gear motor 53 to move supporting sleeve 42 from the top limit position to the bottom limit position.

As cam profiles 63 are detached from projection 64 on supporting sleeve 42, retaining elements 60 are prevented from moving into the lock configuration by locking flanges 62 resting on slip sleeve 76 of adapter 71 (FIG. 9).

As supporting sleeve 42 reaches the bottom limit position (FIG. 10), however, locking flanges 62 of retaining elements 60 click inside the gap between shoulder 39 on supporting sleeve 42 and the top axial end of needle support 33.

At this point, the rotation direction of gear motor 53 is inverted, and supporting sleeve 42 moves into the top limit position. As it does so, needle support 33 and needle 25 remain in the position in which they are retained by locking flanges 62, and are thus withdrawn axially from supporting sleeve 42 and cartridge 4.

As supporting sleeve 42 reaches the top limit position, retaining elements 60 are again parted, and injection device 1 is ready to be fitted with another needle 25 for the next injection.

When using needle box 75 (FIG. 11), this is simply inserted by the mouth end inside opening 30 to activate presence sensor 67 and automatically remove needle 25 from cartridge 4 in exactly the same way as described relative to adapter 71.

The advantages of injection device 1 according to the present invention will be clear from the foregoing description.

In particular, by permitting control of the movement of cartridge 4 to and from contact surface 16, injection device 1 provides for fully automatically fitting and removing needle 25 to/from cartridge 4, and controlling the speed at which needle 25 penetrates the patient's skin.

In other words, when the actual injection is performed, it is possible to set not only the medication dose and the speed at which the dose is delivered, but also the speed at which needle 25 is ejected from housing 2, and therefore skin penetration speed.

Clearly, changes may be made to injection device 1 as described and illustrated herein without, however, departing from the scope of the accompanying Claims.

In particular, the movement of cartridge 4 and delivery of the medication contained in cartridge 4 may be controlled using a single gear motor, which may, for example, by means of a transmission similar to those described, control axial displacement of the core of a Bowden-type flexible cable acting on plunger 27 of cartridge 4; and releasable locking means may be provided for selectively making plunger 27 and body 23 of cartridge 4 integral with each other, so that, when the locking means are activated, cartridge 4 is moved to and from contact surface 16, and, when the locking means are released, plunger 27 slides inside body 23 of cartridge 4 to deliver the medication.

Furthermore, injection device 1 can be used, in the same way as disclosed, with other types of medication containers, such as a syringe.

FIGS. 13-16 show a hand-held, electronically controlled injection device 80 according to a second embodiment of the invention. Like the injection device 1 according to the first embodiment, the injection device 80 shown in FIGS. 13-16 comprises, inside a housing 81 (shown in FIGS. 13, 14 only), a cartridge holder 82 for accommodating a cartridge 83 containing a liquid medication, a push member 84 designed to act on a plunger 85 of cartridge 83, a first electromechanical actuator assembly 86 for driving push member 84 and a second electromechanical actuator assembly 87 for axially moving, in particular, cartridge holder 82. A door 88 provided on a side wall of housing 81, and actuated by a sliding button 89 provided on the same side wall, may be opened by being rotated about a pivot axis 90 to insert or remove a cartridge 83 into/from the injection device. Cartridge holder 82 is axially movable relative to door 88 but rotatable with door 88 about pivot axis 90 when in an axial retracted position.

Push member 84 comprises an axially incompressible and laterally flexible tube 91, having the form of a spring, and deflected by 180° by a guiding rigid semi-circular housing 92 at an upper part of the device, and a piston 93 fixed to an end of tube 91 projecting from housing 92 along the axis B of cartridge holder 82 and cartridge 83. Piston 93 is designed to cooperate with plunger 85 of cartridge 83 (see FIG. 16) as well as with a movable recessed part 94 (see FIG. 15) the function of which will be explained later on.

Figure 15:
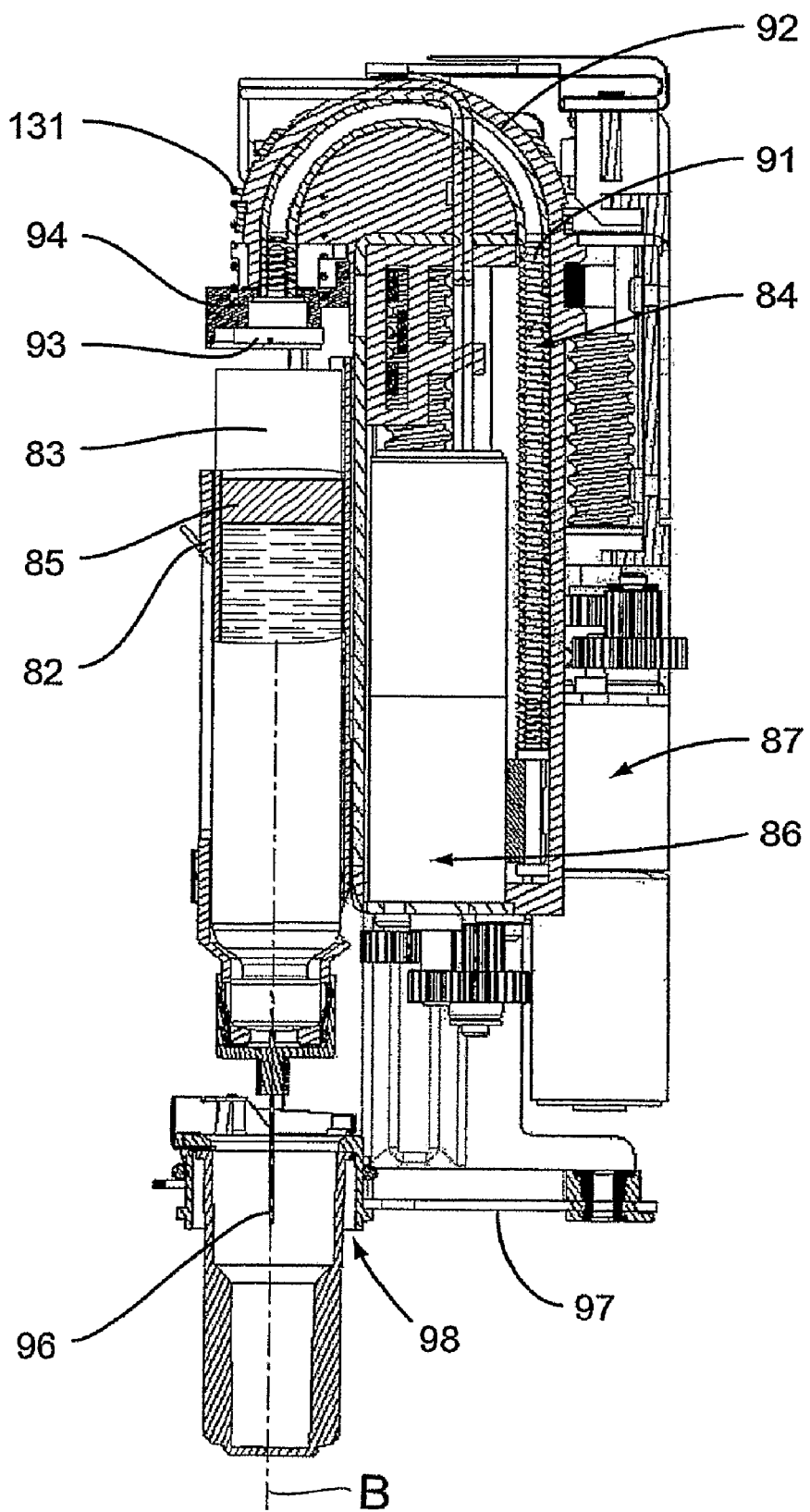
FIGS. 15 and 16 are section views of the interior of the injection device according to the second embodiment, showing two different positions of a push member of the device.
Figure 16:
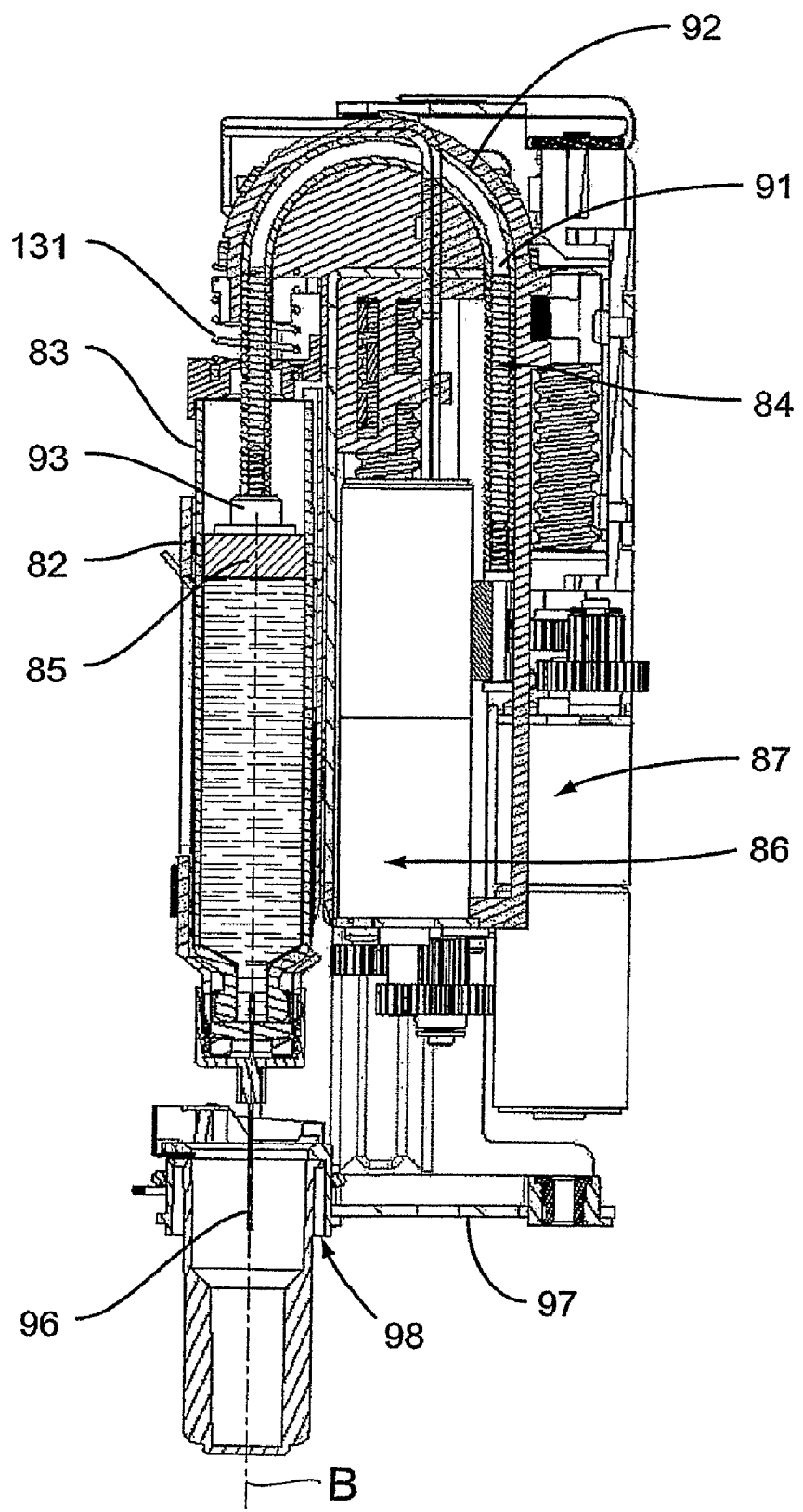
Figure 41:
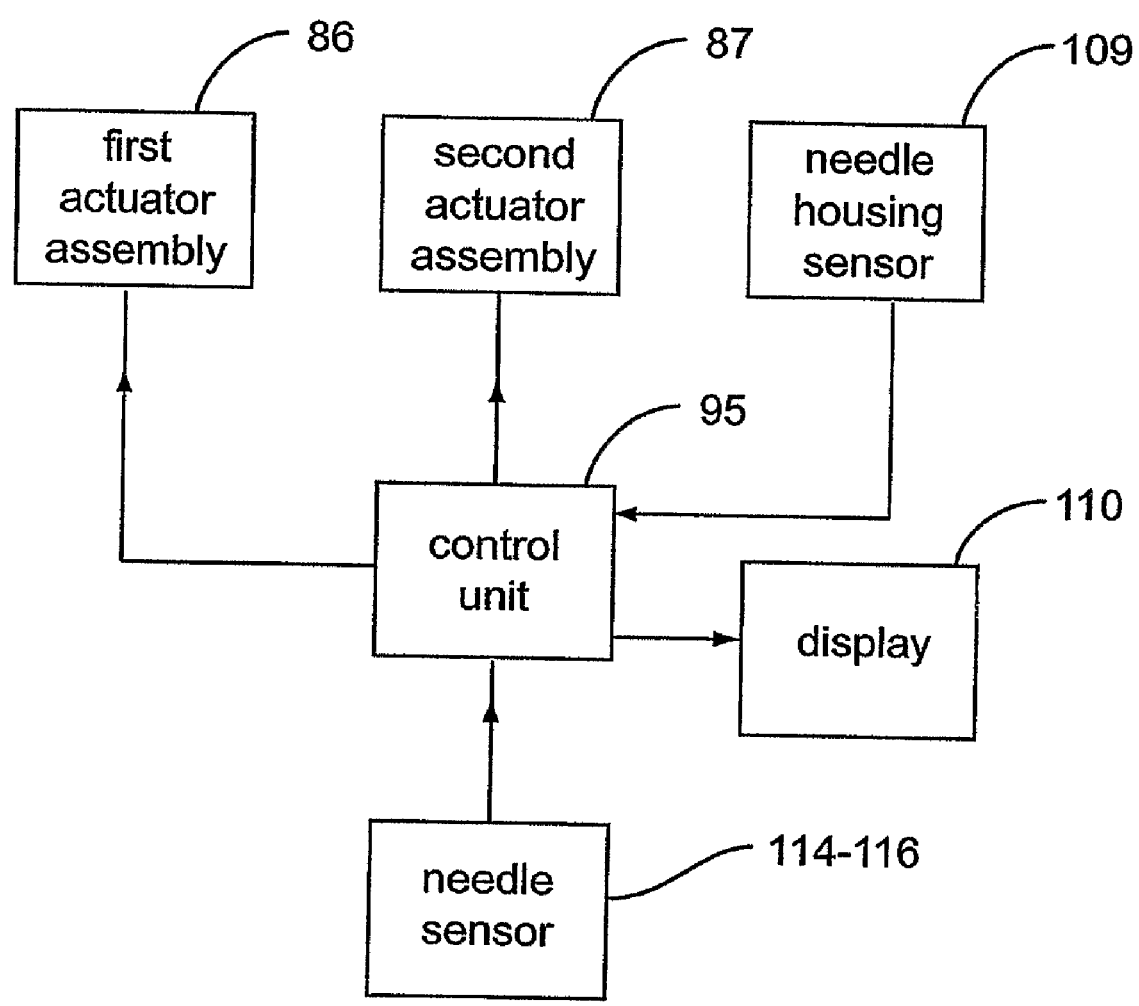
FIG. 41 is a block diagram illustrating operation of a control unit for controlling the injection device according to the second embodiment.

Under the control of a control unit 95, represented in FIG. 41, first actuator assembly 86 may move push member 84 axially from a retracted position, in which piston 93 is outside cartridge 83 and within recessed part 94 (FIG. 15), towards a disposable needle 96 connected to cartridge 83, so that piston 93 comes into contact with plunger 85 within cartridge 83 and pushes plunger 85 to deliver medication through needle 96 (FIG. 16). Push member 84 may then be moved back to its retracted position, leaving plunger 85 at the position it was pushed to.

Second actuator assembly 87 may be controlled by control unit 95 to move a structure comprising first actuator assembly 86, push member 84, push member housing 92 and cartridge holder 82 along axis B, i.e. to and from a bottom wall 97 of device housing 81 for contact with the patient's skin, to automatically fit and remove needle 96 to/from cartridge 83 and to insert and remove needle 96 into/from the patient's skin. More precisely, structure 82, 84, 86, 92 may be moved between a top, retracted position in which needle 96 connected to cartridge 83 is within device housing 81, and one or more bottom positions in which needle 96 projects from a through opening 98 provided in bottom wall 97.

Figure 17:
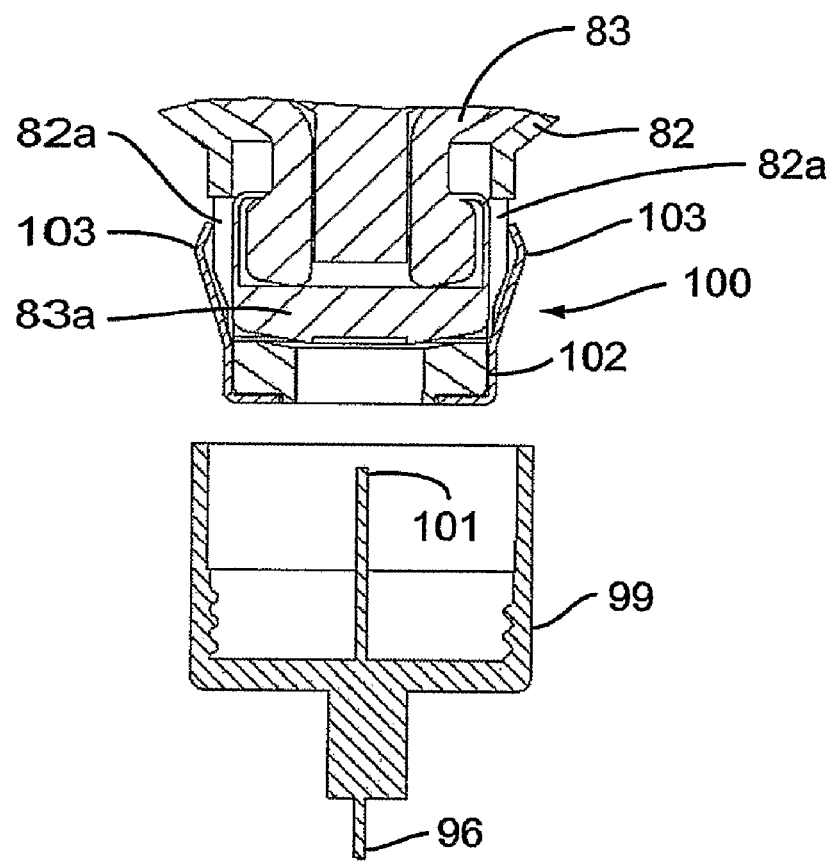
FIGS. 17 and 18 are section views showing a needle and an end of a cartridge inserted in the injection device according to the second embodiment, respectively in a disassembled state and in an assembled state.
Figure 18:
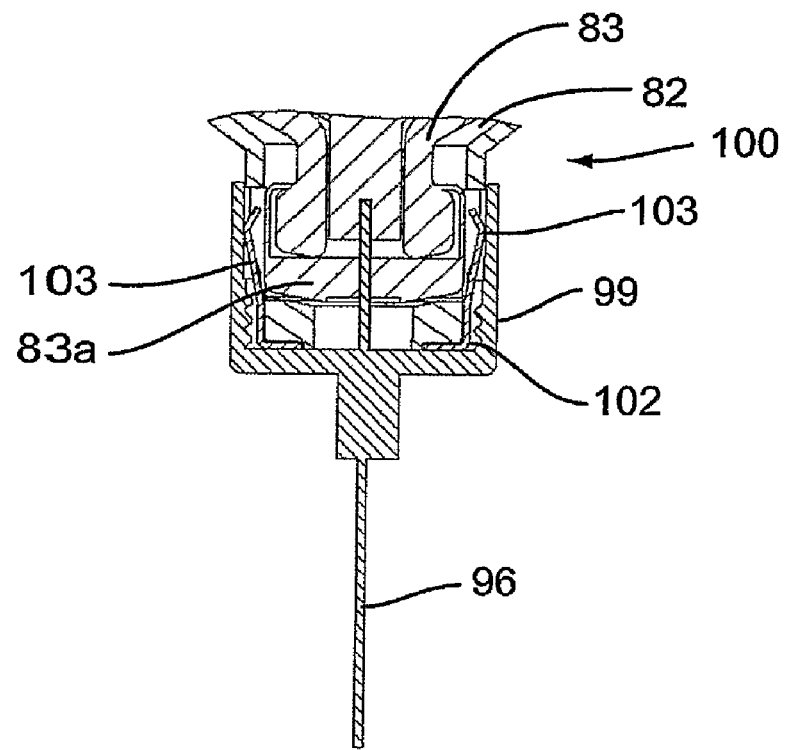

Referring to FIGS. 17, 18, needle 96 is fixed to and projects from a plastic needle support 99 which fits onto a bottom end 100 of cartridge holder 82 so that the corresponding bottom end 83a of cartridge 83, surrounded by bottom end 100, is pierced by the rear end 101 of needle 96. Fitting of needle support 99 onto cartridge holder 82 is achieved by means of an intermediate metal member 102 fixed to bottom end 100 of cartridge holder 82 and having a number of elastic flanges 103 which may be compressed between the external circumferential wall of bottom end 83a of cartridge 83 and the internal circumferential wall of needle support 99 in grooves 82a provided in the cartridge holder wall.

Figure 19:
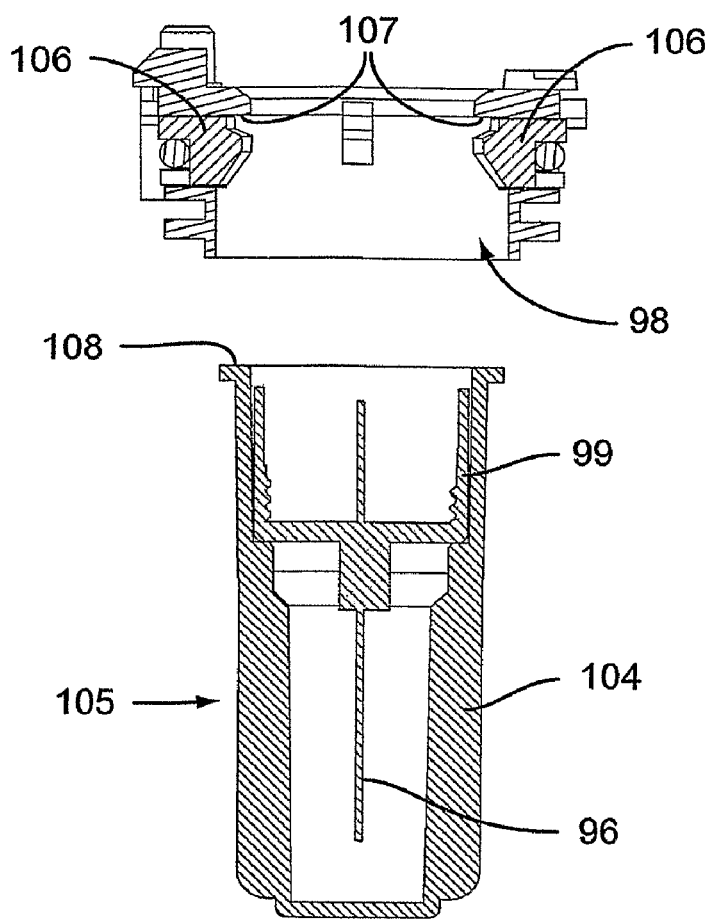
Figure 20:
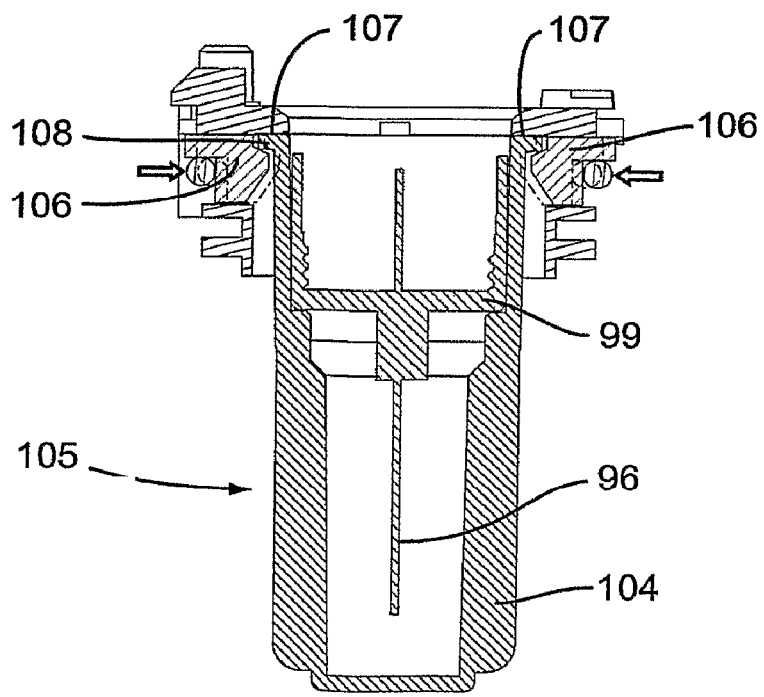

Before connection of needle 96 to cartridge 83, needle support 99, with needle 96, is fitted in a protective needle housing or needle cap 104 and forms with the latter a needle assembly 105 (see FIGS. 19-20).

Referring to FIGS. 19-20, the injection device 80 according to this second embodiment further comprises releasable retaining means for retaining needle assembly 105 in a predetermined position inside opening 98 of bottom wall 97. These releasable retaining means comprise two or more releasable retaining tabs or fingers 106, which are actuated by needle assembly 105 upon its insertion into opening 98, and an axial abutment surface 107 which limits insertion of needle assembly 105 into opening 98. Releasable retaining tabs 106 are disposed on the circumference of opening 98 and are subjected to an elastic load directed towards axis B. With abutment surface 107, releasable retaining tabs 106 define gaps which are engaged by an annular upper flange 108 of needle housing 104 to lock needle assembly 105 in opening 98. An electro-mechanical sensor (electric switch) 109 (FIG. 41), connected to releasable retaining tabs 106, detects actuation of tabs 106 by needle housing 104 and sends an electric signal to control unit 95.

Automatic connection of needle 96 to cartridge 83 is activated by the insertion of needle assembly 105 between tabs 106. This insertion, immediately detected by sensor 109, causes control unit 95 to activate second actuator assembly 87 to move down structure 82, 84, 86, 92 inside device housing 81 from its retracted position. The retaining force exerted by retaining tabs 106 on needle housing 104 is sufficient for needle housing 104 to remain locked in its position shown in FIG. 20 whilst bottom end 100 of cartridge holder 82 equipped with intermediate fixing member 102 engages needle support 99 (FIG. 21). Once movable structure 82, 84, 86, 92 has reached a predetermined bottom position, in which bottom end 100 of cartridge holder 82 fully engages needle support 99, thus connecting needle 96 to cartridge 83, second actuator assembly 87 moves structure 82, 84, 86, 92 back to its top, retracted position with needle support 99 and needle 96 connected to cartridge 83, whilst needle housing 104 is retained by abutment surface 107 (FIG. 22).

Unlike retaining elements 60 in the first embodiment, retaining tabs 106 do not prevent the user from removing needle housing 104 during connection of needle 96 to cartridge 83. However, any removal of needle housing 104 during the connection process is detected by sensor 109. If such a removal occurs, control unit 95 immediately stops the connection process and controls the return of movable structure 82, 84, 86, 92 to its top position. The user will then be proposed, via a display screen 110 (FIG. 41) provided on the injection device, to start a new connection process.

Figure 23:
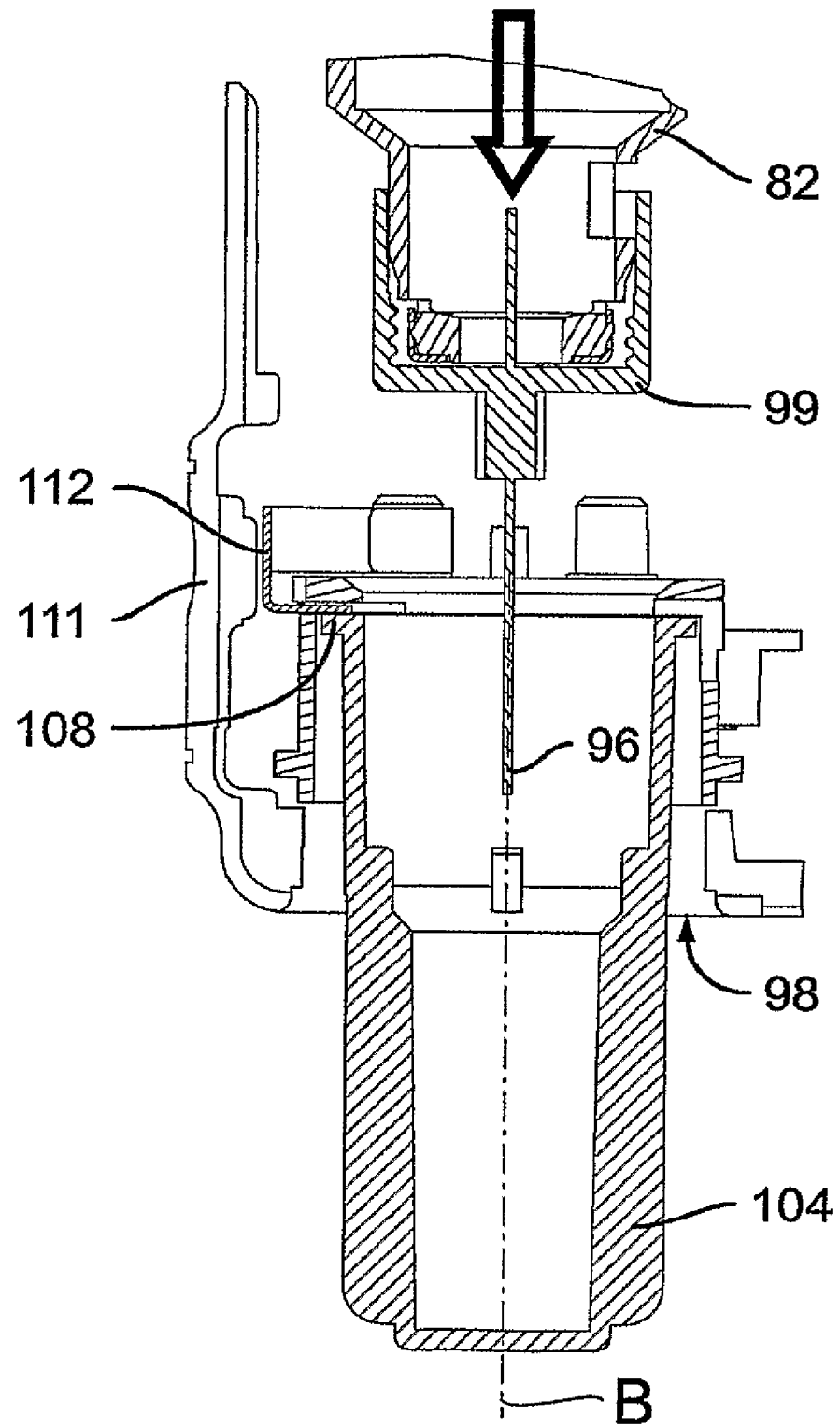

For detaching needle 96 from cartridge 83, the user inserts the empty needle housing 104 into opening 98 up to engagement of retaining means 106, 107 by needle housing 104. Actuation of tabs 106 is detected by sensor 109. This causes control unit 95 to activate second actuator assembly 87 to move structure 82, 84, 86, 92 down to a bottom position where needle support 99 is fitted in needle housing 104 (FIGS. 23, 24). The user may then actuate a needle release button 111 provided on device housing 81 and connected to control unit 95, to move a square retaining member 112 transversely to axis B up to a position where a leg 113 of retaining member 112, inserted in a gap between abutment surface 107 and annular upper flange 108 of needle housing 104, is above the upper end of needle support 99 (FIG. 24). Thereafter, a reverse movement is imparted to structure 82, 84, 86, 92 while needle support 99 and, with it, needle 96 are retained by retaining member 112, thereby detaching needle support 99 and needle 96 from cartridge holder 82 and cartridge 83 (FIG. 25). The user can then disengage needle assembly 105 from retaining tabs 106 and take it out of the injection device.

According to an advantageous aspect of the invention, sensor means are provided in the injection device to detect connection of needle 96 to cartridge 83. These sensor means, visible in FIGS. 26-29, comprise an optical transmitter 114, such as a light-emitting diode, and first and second optical receivers 115, 116, such as photodiodes, fixed to the interior face of the front or the back wall of device housing 81, and a reflector 117, such as a mirror, fixed to the opposite, back or front wall of device housing 81. Optical transmitter 114 is aligned with first and second optical receivers 115, 116 in a direction parallel to axis B and placed between them. When cartridge holder 82, more precisely movable structure 82, 84, 86, 92, is in the retracted position and no needle is connected to cartridge 83 (FIG. 26), a first optical ray 118 forming part of a beam transmitted by transmitter 114 passes a first time near bottom end 100 of cartridge holder 82, is reflected by mirror 117 and passes a second time near bottom end 100 to reach first receiver 115, and a second optical beam 119 transmitted by transmitter 114 passes a first time near bottom end 100, is reflected by mirror 117 and passes a second time near bottom end 100 to reach second receiver 116. As apparent in FIG. 27, the cross-section of an upper portion of bottom end 100 of cartridge holder 82 is only partly circular, i.e. bottom end 100 has a truncated, flat side portion 120, to let first optical beam 118 pass. When needle support 99, with needle 96, is properly connected to bottom end 100 of cartridge holder 82, optical beams 118, 119 are interrupted by needle support 99 (FIG. 29). Receivers 115, 116 thus no longer receive optical beams 118, 119. This is interpreted by control unit 95 as implying that a needle 96 is properly connected to cartridge 83. FIG. 28 shows an intermediate configuration where needle support 99 and needle 96 are only partly connected to cartridge holder 82 and cartridge 83. In this configuration, the second optical beam 119 is interrupted by needle support 99 but the first one, 118, still reaches first receiver 115. This is interpreted by control unit 95 as implying that needle 96 is only partly connected to cartridge 83.

Thus, after the needle connection process described above, if control unit 95 determines that no needle is connected to cartridge 83 or that a needle is only partly connected to cartridge 83, the user is not allowed to initiate the injection and is proposed to restart the needle connection process. Security of use of the injection device is thus increased.

Figure 30:
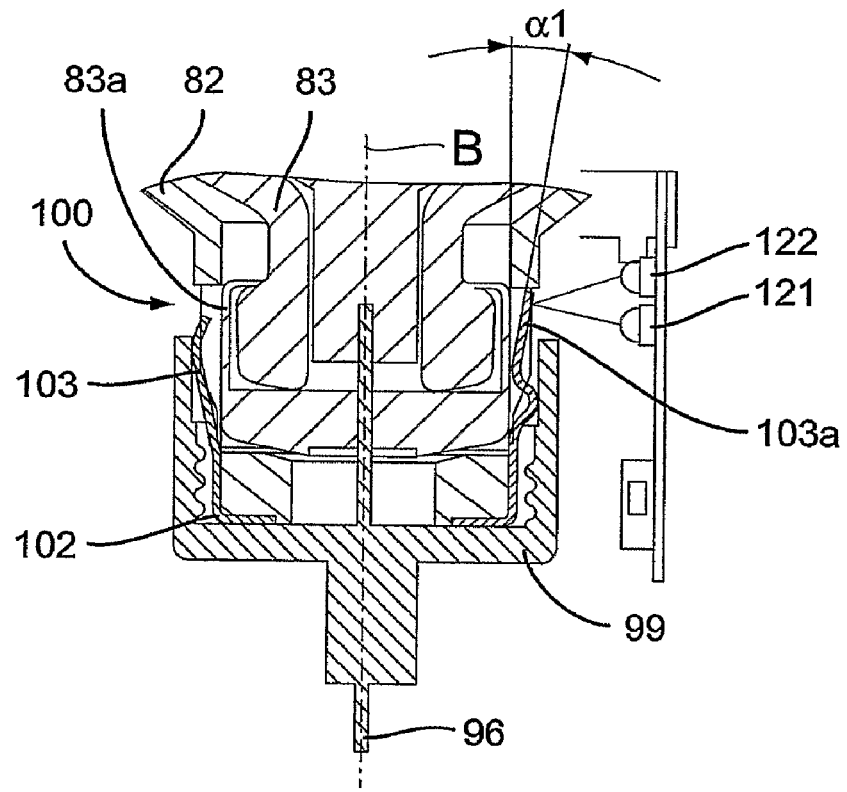
FIGS. 30 and 31 show alternative sensor means for sensing connection of the needle to the cartridge.
Figure 31:
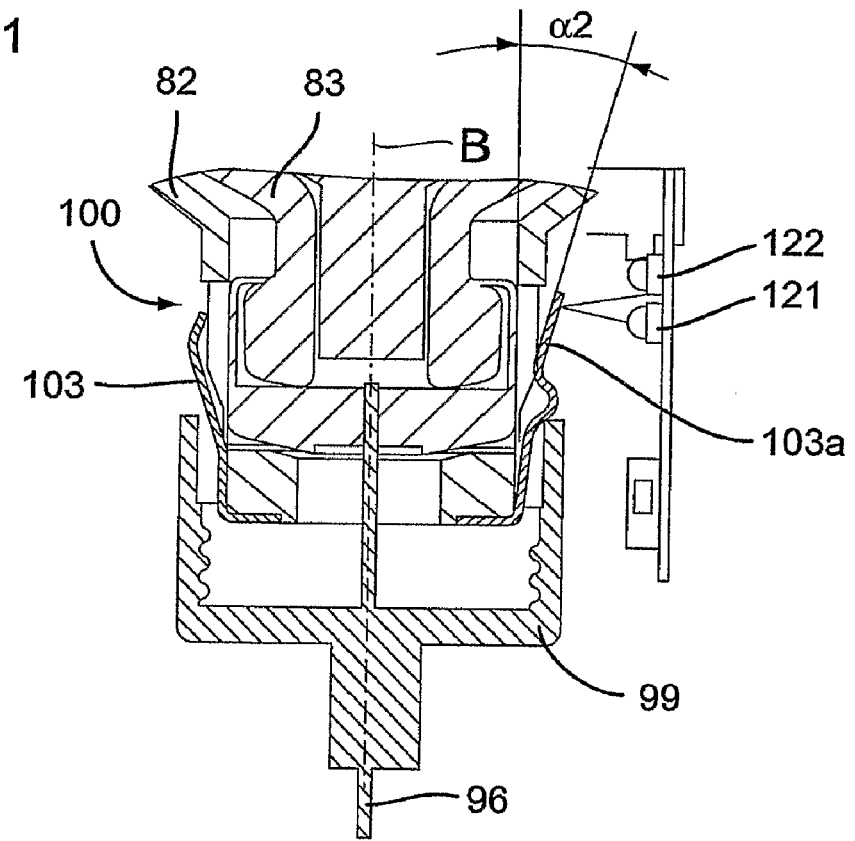
Figure 32:
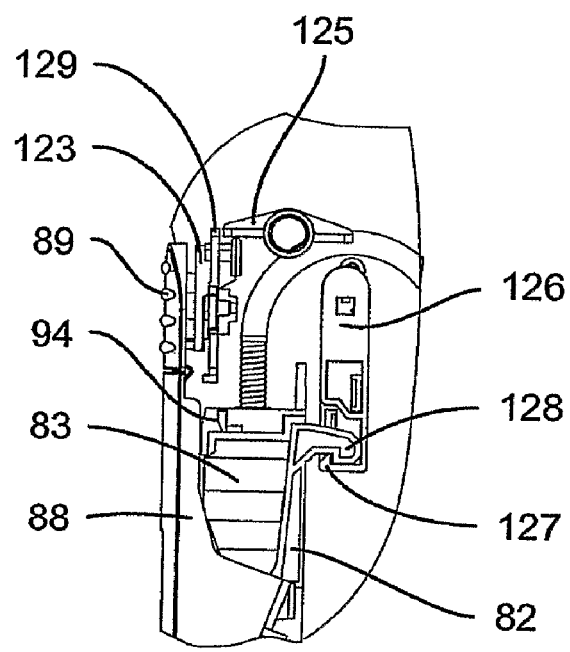
FIGS. 32 to 34 are respectively a front view, a side view and a partially cut side view with parts removed for clarity, of a portion of the injection device according to the second embodiment including a door opening mechanism and a door lock mechanism in a first configuration.
Figure 33:
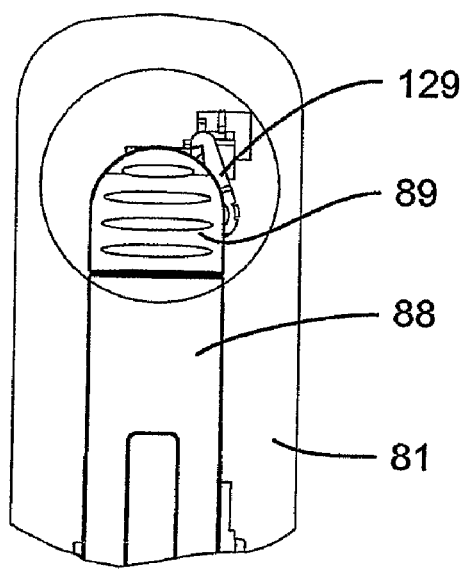
Figure 34:
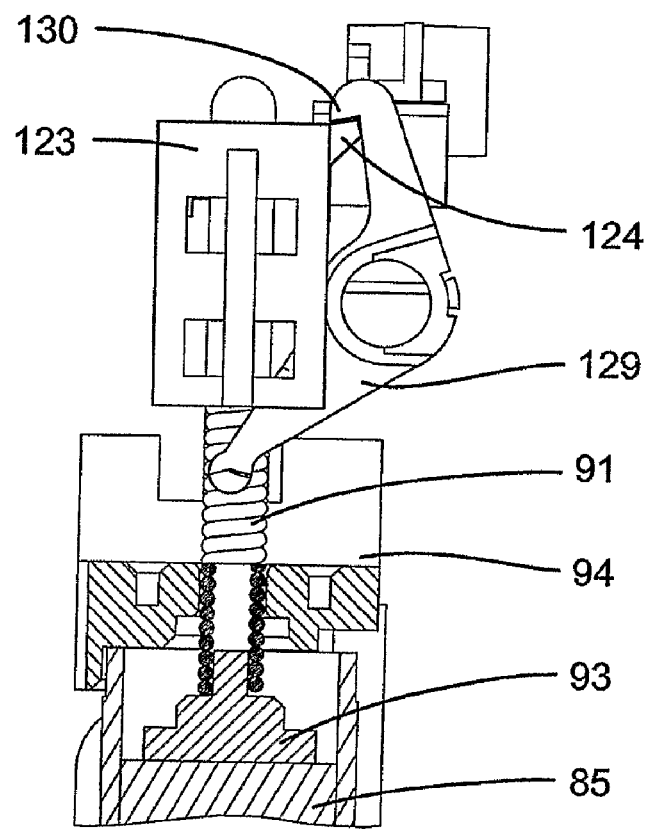

FIGS. 30 and 31 show alternative sensor means for detecting connection of needle 96 to cartridge 83. In this variant, one, 103a, of the elastic flanges 103 of intermediate fixing member 102 is longer than the other(s). When cartridge holder 82 is in the retracted position and needle 96 is properly connected to cartridge 83, the longest elastic flange 103a, compressed between needle support 99 and bottom end 83a of cartridge 83, has an end portion which projects outside needle support 99 and defines a first angle $\alpha 1$ with axis B. In this configuration, an optical ray transmitted by an optical transmitter 121 is reflected by the projecting end portion of flange 103a towards an optical receiver 122. Reception of a signal by optical receiver 122 is interpreted by control unit 95 as implying that needle 96 is properly connected to cartridge 83. If, on the other hand, needle 96 is not properly connected to cartridge 83, as shown in FIG. 31, then the projecting end portion of flange 103a defines a second angle $\alpha 2$, different from the first angle $\alpha 1$, with axis B. In this case, the optical ray reflected by the projecting end portion of flange 103a is not received by receiver 122. This is interpreted by control unit 95 as implying that no needle is connected to cartridge 83 or that a needle is ill connected to cartridge 83.

Returning to FIGS. 15 and 16, delivery of medication through needle 96 is, as explained above, carried out by piston 93 of push member 84 pushing plunger 85 of cartridge 83. During this process, piston 93 and a portion of tube 91 is within cartridge 83. Piston 93 and tube 91 remain within cartridge 83 so long as doses of medication are left therein. Once all doses of medication contained in cartridge 83 have been injected into a patient, push member 84 is retracted outside cartridge 83 to enable replacement of the latter (FIG. 15). A risk could however exist that, between two injections, the user opens door 88 to remove cartridge 83 from the injection device whilst push member 84 is still inside cartridge 83. Such an operation could seriously damage push member 84.

In order to eliminate this risk, the present invention advantageously provides a lock mechanism which locks/unlocks the opening mechanism of door 88 when push member 84 is inside/outside cartridge 83.

With reference to FIGS. 32-40, the opening mechanism of door 88 comprises opening button 89, which is slidable in a direction parallel to axis B, a lockable part 123 fixed to opening button 89 inside device housing 81 and comprising a flange 124, a lever 125 actuated by lockable part 123 and a locking member 126 actuated by lever 125. Lever 125 is mounted on an axis that is fixed relative to device housing 81. Locking member 126 is mounted on movable structure 82, 84, 86, 92 at a location situated on the opposite side of axis B with respect to opening button 89 and so as to be slidable with respect to movable structure 82, 84, 86, 92 in a direction parallel to axis B, and has a recess with a flange 127 designed to cooperate with a corresponding flange 128 of cartridge holder 82.

The lock mechanism comprises movable recessed part 94 and a lever 129 actuated by recessed part 94 and having, at one of its end, a flange 130 designed to cooperate with flange 124 of lockable part 123. Lever 129 is mounted on an axis that is fixed relative to device housing 81. Recessed part 94 is movable along axis B and fixed to one end of a spring 131 (visible in FIGS. 13-16) the other end of which is fixed to movable structure 82, 84, 86, 92.

Figure 35:
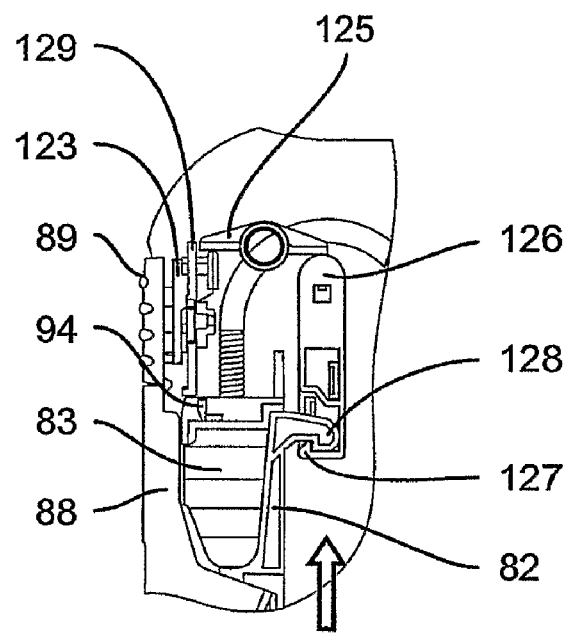
FIGS. 35 to 37 are respectively a front view, a side view and a partially cut side view with parts removed for clarity, of the portion of the injection device according to the second embodiment including the door opening mechanism and the door lock mechanism in a second configuration.
Figure 36:
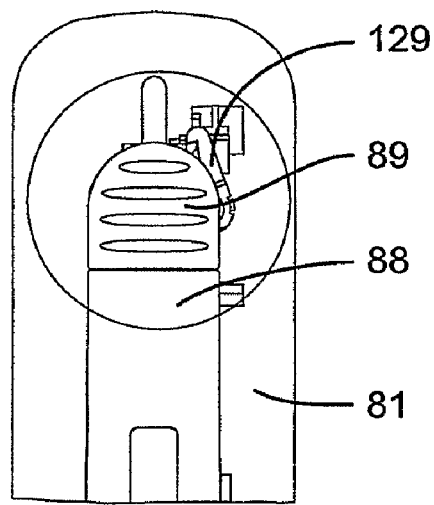
Figure 37:
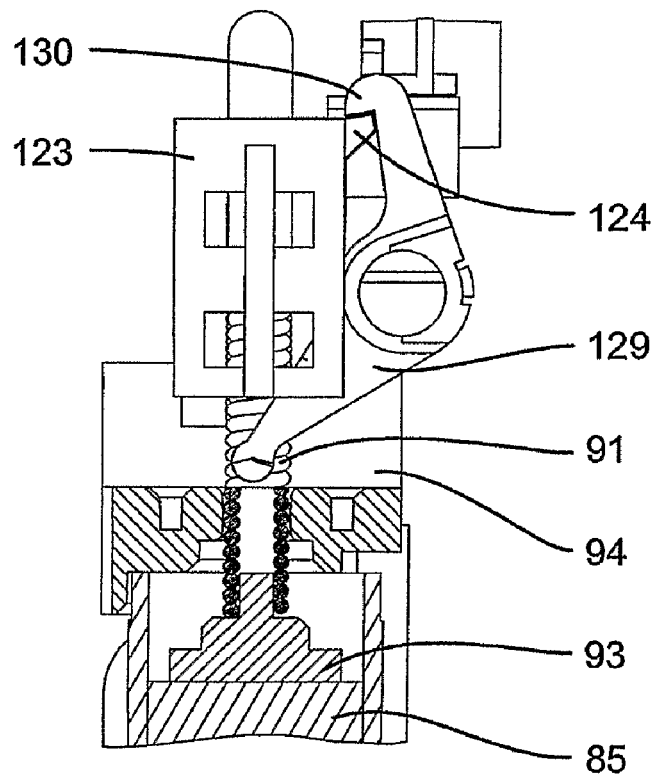
Figure 38:
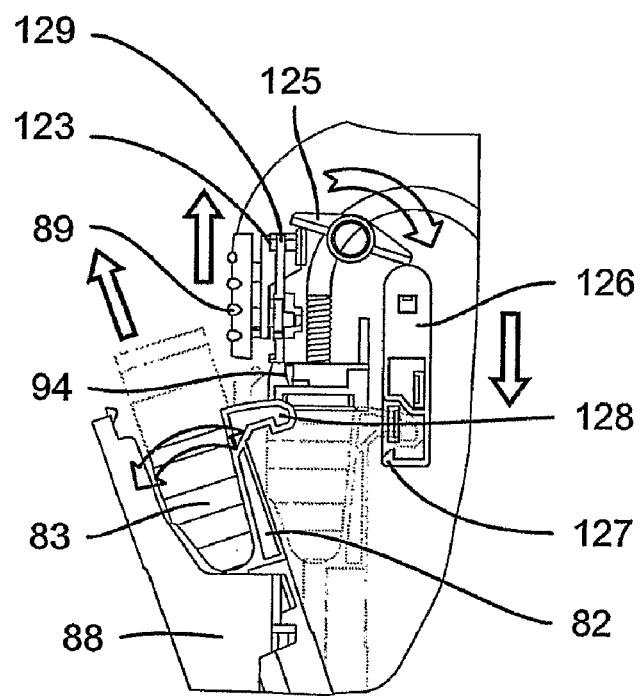
FIGS. 38 to 40 are respectively a front view, a side view and a partially cut side view with parts removed for clarity, of the portion of the injection device according to the second embodiment including the door opening mechanism and the door lock mechanism in a third configuration.
Figure 39:
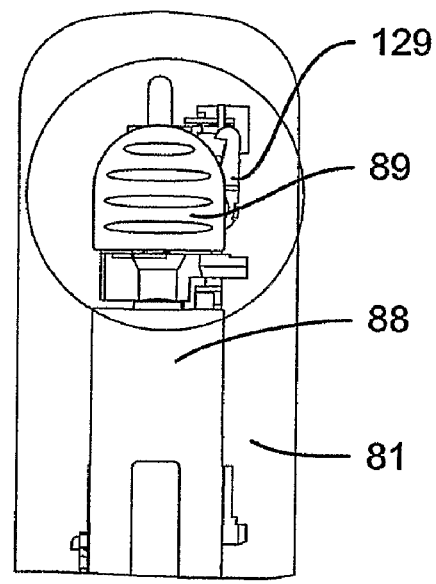
Figure 40:
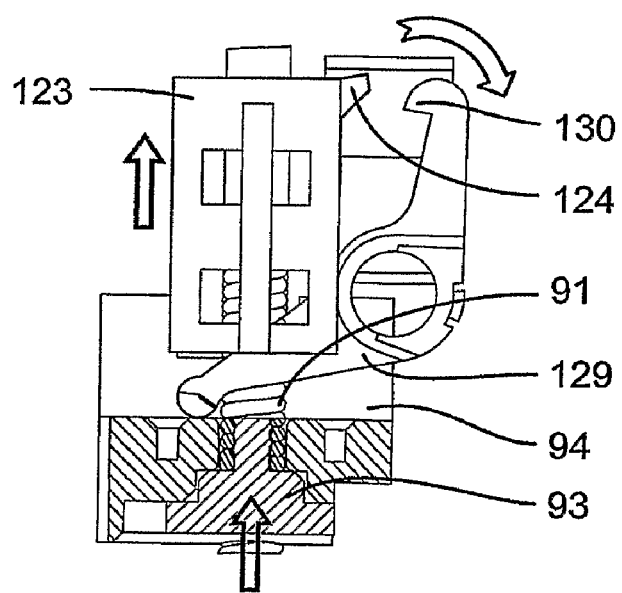

Operation of the opening and lock mechanisms is as follows: during injection of a medication dose (FIGS. 32-34), movable structure 82, 84, 86, 92 is in a bottom position, piston 93 of push member 84 is inside cartridge 83 and recessed part 94 is in a rest position, out of contact with lever 129. In this configuration, flange 130 of second lever 129 engages flange 124 of lockable part 123 (FIGS. 33, 34) so that lockable part 123 and, with it, opening button 89 are locked, i.e. cannot be moved up, thus preventing door 88 from being opened. Between two injections with the same cartridge 83, movable structure 82, 84, 86, 92 is in its retracted position, piston 93 of push member 84 is inside cartridge 83 and recessed part 94 is in a rest position, out of contact with lever 129 (FIGS. 35-37). In this configuration, flange 130 of second lever 129 still engages flange 124 of lockable part 123 (FIG. 37) so that lockable part 123 and, with it, opening button 89 remain locked, thus preventing door 88 from being opened. Once all medication doses contained in cartridge 83 have been injected, movable structure 82, 84, 86, 92 and piston 93 of push member 84 are each retracted. During retraction of push member 84, piston 93 enters the recess of recessed part 94 and pushes recessed part 94 upwards against the action of spring 131 so that recessed part 94 comes into contact with the end of second lever 129 opposite to the end having flange 124 to rotate lever 129 and thus disengage it from lockable part 123 (FIG. 40). Door opening button 89 may then be slid upwards as shown in FIG. 38. Upwards motion of opening button 89 causes first lever 125 to rotate to move locking member 126 down and thus disengage flange 128 of cartridge holder 82 from flange 127 of locking member 126. Under the action of a spring, door 88 and, with it, cartridge holder 82 are then rotated about pivot axis 90 to enable extraction of cartridge 83 from cartridge holder 82 (FIG. 38). Door opening button 89, lever 125, locking member 126 and lever 129 are subjected to the action of respective springs which tend to maintain them in their rest position shown in FIGS. 32 to 34 or 35 to 37.

The invention claimed is:

1. A hand-held, electronically controlled injection device for injecting preset doses of a liquid medication, comprising a housing adapted to receive a medication container containing the liquid medication and which has a contact surface adapted to contact a patient's skin, wherein said contact surface comprises a through opening adapted to receive a needle assembly comprising a needle;

electromechanical actuator means configured to move said medication container within said housing to and from said contact surface;

retaining means configured to selectively lock said needle assembly at a locked position at said through opening, wherein said electromechanical actuator means and said retaining means are configured to allow automatic connection of said needle to said medication container by moving said medication container towards said contact surface from a first operating position withdrawn inside said housing to a second operating position while said retaining means maintains said needle assembly at said locked position.

2. A device as claimed in claim 1, comprising presence sensor means configured to generate a presence signal to activate said electromechanical actuator means upon said needle assembly engaging said opening.

3. A device as claimed in claim 1, wherein said retaining means comprise at least one locking lever movable between a lock configuration, in which a respective work portion projects inside said opening to interact with said needle assembly, and a release configuration, in which said work portion is located outside said opening.

4. A device as claimed in claim 3, wherein said locking lever is loaded elastically into the lock configuration; and a push means is configured to set said locking lever to said release configuration at least in said first operating position of said medication container.

5. A device as claimed in claim 4, wherein said push means comprise cam means interposed between said locking lever and a support configured to support said medication container and which is movable to and from said contact surface.

6. A device as claimed in claim 1, comprising removing means configured to remove said needle from said medication container; said removing means comprising stop means configured to be selectively activated in a third operating position of said medication container, close to said second operating position, to lock said needle and disconnect said needle from said medication container as said medication container moves into said first operating position.

7. A device as claimed in claim 6, wherein said third operating position is located on the opposite side of said second operating position with respect to said first operating position in a travelling direction of said medication container.

8. A device as claimed in claim 6, wherein said retaining means comprise at least one locking lever movable between a lock configuration, in which a respective work portion projects inside said opening to interact with said needle assembly, and a release configuration, in which said work portion is located outside said opening, wherein said needle assembly comprises a needle support supporting said needle in projecting manner and connectable to one end of said medication container, and wherein, in said third operating position of said medication container, said work portion of said locking lever is interposable between said medication container and said needle support to define said stop means.

9. A device as claimed in claim 1, wherein said retaining means comprise at least one releasable retaining member configured to be actuated by said needle assembly upon insertion of said needle assembly into said opening, said releasable retaining member(s) configured to retain said needle assembly at least during said displacement of said medication container from said first to said second operating position.

10. A device as claimed in claim 9, comprising means for removing said needle from said medication container, said removing means comprising stop means which may be activated in said second operating position of said medication container to retain said needle and disconnect said needle from said medication container as said medication container is moved from said second to said first operating position.

11. A device as claimed in claim 1, wherein said needle assembly comprises a needle support configured to support said needle, and wherein at least one of said needle support and an end of a medication container unit, comprising said medication container and a holder holding said medication container located inside said housing, is provided with at least one elastic flange for connection of said needle support to said end of said medication container unit.

12. A device as claimed in claim 1, comprising first sensor means configured to detect proper connection of said needle to said medication container.

13. A device as claimed in claim 12, wherein said first sensor means comprise optical transmitter means and first optical receiver means arranged so that, when no needle is properly connected to said medication container, a first optical ray transmitted by said transmitter means passes near an end of a medication container unit, comprising said medication container and a holder holding said medication container inside said housing, to reach said first receiver means, and when said needle is properly connected to said medication container, said first optical ray is interrupted by a needle support supporting said needle.

14. A device as claimed in claim 13, wherein said end of said medication container unit is truncated to let said first optical ray pass when no needle is properly connected to said medication container.

15. A device as claimed in claim 12, comprising second sensor means for detecting partial connection of said needle to said medication container.

16. A device as claimed in claim 13, comprising a second sensor means configured to detect partial connection of said needle to said medication container, and wherein said second sensor means comprise said optical transmitter means and second optical receiver means arranged so that, when no needle is connected to said medication container, a second optical ray transmitted by said transmitter means passes near said end of said medication container unit to reach said second receiver means, and in a configuration where said needle is partly connected to said medication container, said second optical ray is interrupted by said needle support while said first optical ray still reaches said first receiver means.

17. A device as claimed in claim 12, wherein an end of a medication container unit, comprising said medication container and a holder configured to hold said medication container inside said housing, is provided with at least one elastic flange for connection of a needle support supporting said needle to said end of said medication container unit, and wherein said first sensor means comprise optical transmitter means and optical receiver means arranged so that, when said needle is properly connected to said medication container, a reflective portion of one of said elastic flange(s) reflects an optical ray transmitted by said transmitter means towards said receiver means, and when no needle is properly connected to said medication container, said reflective portion reflects said optical ray in a direction not corresponding to said receiver means.

18. A device as claimed in claim 1, comprising second actuator means configured to be selectively activated to force the liquid medication contained in said medication container through a patient's skin.

19. A device as claimed in claim 18, wherein said second actuator means comprise an actuator assembly and a push member configured to be driven by said actuator assembly and which can be moved axially from a retracted position, located outside said medication container, to enter said medication container and push the liquid medication out of said medication container through said needle, and then returned to its retracted position, said device further comprising a door which, in its open position, is configured to permit insertion or removal of said medication container into or from said housing, a door opening mechanism configured to open or close said door and a lock mechanism configured to lock at least part of said door opening mechanism, to prevent opening of said door, when said push member is located inside said medication container and configured to unlock said door opening mechanism when said push member is in said retracted position.

20. A device as claimed in claim 19, wherein said lock mechanism is designed to lock a door opening button of said door opening mechanism when said push member is inside said medication container.

21. A device as claimed in claim 20, wherein said lock mechanism comprises a first lever configured to lock said door opening button when in a rest position, said first lever configured to be actuated by said push member during retraction of this latter to unlock said door opening button.

22. A device as claimed in claim 21, wherein said lock mechanism further comprises a part movable in the direction of displacement of said push member and which, in a rest position, is out of contact with said first lever and, during retraction of said push member, is pushed by an end portion of said push member to come into contact with and actuate said first lever.

23. A device as claimed in claim 19, wherein said door opening mechanism comprises a door opening button movable in the direction of displacement of said push member, a second lever actuated by said door opening button, a locking member movable in said direction, actuated by said second lever and having a first flange, and a medication container holder configured to hold said medication container inside said housing, said medication container holder having a second flange designed to cooperate with said first flange and being pivotable with said door from a closed to an open position of said door when said second flange is released by said first flange.

24. A device as claimed in claim 18, comprising injection control button means, said button means configured to successively activate said electromechanical actuator means to move the assembly defined by the medication container and needle from the first to the second operating position so that the needle penetrates the patient's skin, and said second actuator means to deliver through the patient's skin a preset dose of liquid medication contained in said medication container.

25. A device as claimed in claim 24, comprising skin sensor means configured to generate a consent signal to activate said button means upon interaction between said contact surface and the patient's skin.

26. A device as claimed in claim 24, comprising selecting means configured to select a speed at which said medication container moves towards said contact surface at least as said needle penetrates the patient's skin, said selecting means configured to set a dose of liquid medication to be injected into the patient.

27. A device as claimed in claim 1, comprising said needle assembly.

28. A device as claimed in claim 1, wherein said needle assembly comprises at least one needle housing fitted to said needle, and wherein said retaining means is adapted to lock said needle housing both during displacement of said medication container from said first to said second operating position and during a reverse displacement of said medication container from said second to said first operating position to permit automatic withdrawal of said needle from said needle housing.

29. A device as claimed in claim 28, wherein said retaining means comprise at least one releasable retaining member configured to be actuated by said needle housing upon insertion of said needle housing into said opening, said releasable retaining member configured to retain said needle housing at least during said displacement of said medication container from said first to said second operating position, and wherein said retaining means further comprise an abutment surface configured to limit insertion of said needle housing into said opening and to retain said needle housing during said reverse displacement of said medication container from said second to said first operating position.

30. A device as claimed in claim 29, comprising sensor means configured to sense actuation of said releasable retaining member.

31. A device as claimed in claim 30, comprising means for reversing displacement of said medication container immediately after said sensor means have detected a disengagement of said needle housing from said releasable retaining member(s) during said displacement of said medication container from said first to said second operating position.

* * * * *